(12) United States Patent
Dodier et al.

(10) Patent No.: US 7,851,500 B2
(45) Date of Patent: Dec. 14, 2010

(54) AMINOPYRAZOLE KINASE INHIBITORS

(75) Inventors: Marco Dodier, Wotton (CA); Claude A. Quesnelle, Skillman, NJ (US); Anne Marinier, Kirkland (CA)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/521,061

(22) PCT Filed: Jan. 4, 2008

(86) PCT No.: PCT/US2008/050157

§ 371 (c)(1),
(2), (4) Date: Oct. 2, 2009

(87) PCT Pub. No.: WO2008/086128

PCT Pub. Date: Jul. 17, 2008

(65) Prior Publication Data

US 2010/0022503 A1    Jan. 28, 2010

Related U.S. Application Data

(60) Provisional application No. 60/883,601, filed on Jan. 5, 2007.

(51) Int. Cl.
*C07D 403/02* (2006.01)
*A01N 43/56* (2006.01)

(52) U.S. Cl. ...................... 514/407; 548/364.7
(58) Field of Classification Search ............ None
See application file for complete search history.

(56) References Cited

FOREIGN PATENT DOCUMENTS

WO   WO 2004/009601   1/2004

OTHER PUBLICATIONS

Bender et al., caplus an 2004:905786.*
Dayam, et al., Expert Opinion on Therapeutic Patents, vol. 17, No. 1, pp. 83-102 (2007).

* cited by examiner

*Primary Examiner*—Sun Jae Y. Loewe
(74) *Attorney, Agent, or Firm*—Elliott Korsen

(57) ABSTRACT

The present invention provides compounds of formula (I) and pharmaceutically acceptable salts thereof. The formula (I) compounds inhibit tyrosine kinase activity thereby making them useful as anticancer agents.

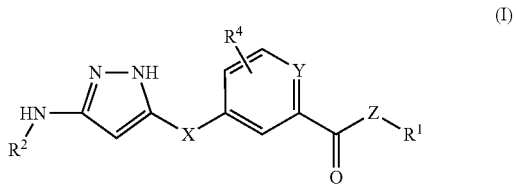

9 Claims, No Drawings

AMINOPYRAZOLE KINASE INHIBITORS

FIELD OF THE INVENTION

This invention relates to novel aminopyrazole compounds that are useful as anti-cancer agents. This invention also relates to a method of using the compounds in the treatment of proliferative diseases such as cancer, and to pharmaceutical compositions containing the compounds.

BACKGROUND

The invention relates to compounds which inhibit tyrosine kinase enzymes, compositions which contain tyrosine kinase inhibiting compounds and methods of using inhibitors of tyrosine kinase enzymes to treat diseases which are characterized by an overexpression or up regulation of tyrosine kinase activity such as cancer, diabetes, restenosis, arteriosclerosis, psoriasis, angiogenic diseases and immunologic disorders (Powis, G.; Workman P. Signaling targets For The Development of Cancer Drugs. *Anti-Cancer Drug Design* (1994), 9: 263-277; Merenmies, J.; Parada, L. F.; Henkemeyer, M. Receptor Tyrosine Kinase Signaling in Vascular Development. *Cell Growth Differ* (1997) 8: 3-10; Shawver, L. K.; Lipsosn, K. E.; Fong, T. A. T.; McMahon, G.; Plowman, G. D.; Strawn, L. M. Receptor Tyrosine Kinases As Targets For Inhibition of Angiogenesis. *Drug Discovery Today* (1997) 2: 50-63; all herein incorporated by reference).

Tyrosine kinases play a critical role in signal transduction for several cellular functions including cell proliferation, carcinogenesis, apoptosis, and cell differentiation (Plowman, G. D.; Ullrich, A.; Shawver, L. K.: Receptor Tyrosine Kinases As Targets For Drug Intervention. *DN&P* (1994) 7: 334-339). Inhibitors of these enzymes are useful for the treatment or prevention of proliferative diseases which are dependent on these enzymes. Strong epidemiologic evidence suggests that the overexpression or activation of receptor protein tyrosine kinases leading to constitutive mitogenic signaling is an important factor in a growing number of human malignancies. Tyrosine kinases that have been implicated in these processes include Abl, CDK's, EGF, EMT, FGF, FAK, Flk-1/KDR, HER-2, IGF-1R, IR, LCK, MET, PDGF, Src, and VEGF. Thus, there is an ongoing need to investigate novel compounds that can be used to regulate or inhibit tyrosine kinase enzymes.

SUMMARY OF THE INVENTION

The invention is directed to compounds of Formula I that inhibit tyrosine kinase enzymes making them useful for the treatment of cancer:

Furthermore, the invention is directed to methods for treating a condition associated with one or more tyrosine kinase inhibitor comprising administering to a mammal in need of such treatment a therapeutically effective amount of a compound of formula I and optionally one or more other anticancer agent.

The invention also provides methods for treating cancer using the compounds of the present invention either alone or together with one or more other anticancer agent.

DETAILED DESCRIPTION OF THE INVENTION

The invention provides for compounds of formula I, pharmaceutical compositions employing such compounds and for methods of using such compounds.

In accordance with the invention, there are disclosed compounds of formula I

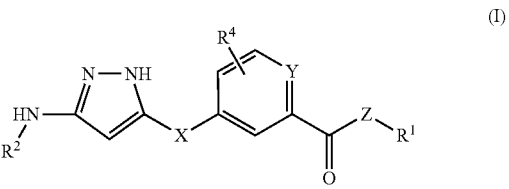

wherein the symbols have the following meanings and are, for each occurrence, independently selected:
X is —O— or —S—;
Y is —N— or —CH—;
Z is —NH— or —O—;
$R^1$ is H, $C_1$-$C_6$ alkyl, $C_1$-$C_5$ arylalkyl, $C_3$-$C_8$ cycloalkyl, $C_9$-$C_{14}$ bicycloalkyl, $C_6$-$C_{10}$ aryl, $C_5$-$C_{13}$ heteroaryl, $C_4$-$C_{12}$ heterocyclyl and 3 to 8-membered heterocycloalkyl and each of said groups is optionally substituted with 1 to 3 groups selected from the group consisting of halogen, —OH, —C(=O)O$R^3$, —S(=O)NH$R^3$, —SO$_2$NH$R^3$, —SO$_2$$R^3$, alkyl, substituted alkyl, —CN, —NH$R^3$, —CONH$R^3$, —OCONH$R^3$, —CONHSO$_2$$R^3$, —NHCONH$R^3$, —CH$_2$O$R^3$, —CH$_2$CH$_2$OH, alkoxy, substituted alkoxy, aryl, substituted aryl, heteroaryl and substituted heteroaryl;
wherein $R^3$ is hydrogen or $C_1$-$C_4$ alkyl; $C_3$-$C_6$ cycloalkyl, $C_6$-$C_{10}$ aryl, substituted aryl, $C_1$-$C_5$ arylalkyl, heteroaryl, heterocyclyl, aryloxy, substituted aryloxy, —CF$_3$ and —OCF$_3$;
$R^2$ is an optionally substituted aryl or heteroaryl group; said substituents on the substituted aryl or substituted heteroaryl group are selected from the group consisting of one or more hydrogen, halogen, alkyl, substituted alkyl, alkoxy, substituted alkoxy, hydroxy, hydroxyalkyl, halogen, haloalkyl, haloalkoxy, amino, substituted amino, aminoalkyl, substituted aminoalkyl, alkylamino, substituted alkylamino, amide, substituted amide and carbamate; and
$R^4$ is hydrogen, alkyl, substituted alkyl, hydroxy, cyano or halogen;
or a pharmaceutically acceptable salt or stereoisomer thereof.

In another embodiment, the invention comprises a compound of formula II wherein

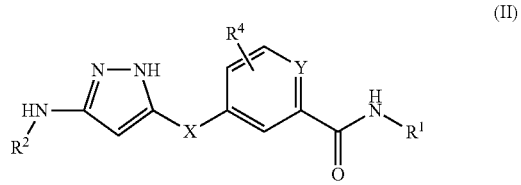

wherein
X is —O— or —S—;
Y is —N— or —CH—;
$R^1$ is H, $C_1$-$C_6$ alkyl, $C_1$-$C_5$ arylalkyl, $C_3$-$C_8$ cycloalkyl, $C_9$-$C_{14}$ bicycloalkyl, $C_6$-$C_{10}$ aryl, $C_5$-$C_{13}$ heteroaryl, $C_4$-$C_{12}$ heterocyclyl and 3 to 8-membered heterocycloalkyl and each of said groups is optionally substituted with 1 to 3 groups selected from the group consisting of halogen, —OH, —C(=O)OR³, —S(=O)NHR³, —SO₂NHR³, —SO₂R³, alkyl, substituted alkyl, —CN, —NHR³, —CONHR³, —OCONHR³, —CONHSO₂R³, —NHCONHR³, —CH₂OR³, —CH₂CH₂OH, alkoxy, substituted alkoxy, aryl, substituted aryl, heteroaryl and substituted heteroaryl;

wherein R³ is hydrogen or C₁-C₄ alkyl; C₃-C₆ cycloalkyl, C₆-C₁₀ aryl, substituted aryl, C₁-C₅ arylalkyl, heteroaryl, heterocyclyl, aryloxy, substituted aryloxy, —CF₃ and —OCF₃;

R² is an optionally substituted aryl or heteroaryl group; said substituents on the substituted aryl or substituted heteroaryl group are selected from the group consisting of one or more hydrogen, halogen, alkyl, substituted alkyl, alkoxy, substituted alkoxy, hydroxy, hydroxyalkyl, halogen, haloalkyl, haloalkoxy, amino, substituted amino, aminoalkyl, substituted aminoalkyl, alkylamino, substituted alkylamino, amide, substituted amide and carbamate; and R⁴ is hydrogen, alkyl, substituted alkyl, hydroxy, cyano or halogen;

or a pharmaceutically acceptable salt or stereoisomer thereof.

In another embodiment, the invention comprises a compound of formula III

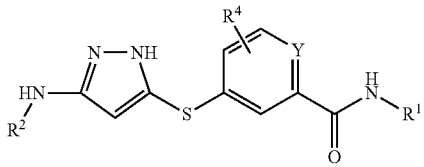

(III)

wherein

Y is —N— or —CH—;

R¹ is H, C₁-C₆ alkyl, C₁-C₅ arylalkyl, C₃-C₈ cycloalkyl, C₉-C₁₄ bicycloalkyl, C₆-C₁₀ aryl, C₅-C₁₃ heteroaryl, C₄-C₁₂ heterocyclyl and 3 to 8-membered heterocycloalkyl and each of said groups is optionally substituted with 1 to 3 groups selected from the group consisting of halogen, —OH, —C(=O)OR³, —S(=O)NHR³, —SO₂NHR³, —SO₂R³, alkyl, substituted alkyl, —CN, —NHR³, —CONHR³, —OCONHR³, —CONHSO₂R³, —NHCONHR³, —CH₂OR³, —CH₂CH₂OH, alkoxy, substituted alkoxy, aryl, substituted aryl, heteroaryl and substituted heteroaryl;

wherein R³ is hydrogen or C₁-C₄ alkyl; C₃-C₆ cycloalkyl, C₆-C₁₀ aryl, substituted aryl, C₁-C₅ arylalkyl, heteroaryl, heterocyclyl, aryloxy, substituted aryloxy, —CF₃ and —OCF₃;

R² is an optionally substituted aryl or heteroaryl group; said substituents on the substituted aryl or substituted heteroaryl group are selected from the group consisting of one or more hydrogen, halogen, alkyl, substituted alkyl, alkoxy, substituted alkoxy, hydroxy, hydroxyalkyl, halogen, haloalkyl, haloalkoxy, amino, substituted amino, aminoalkyl, substituted aminoalkyl, alkylamino, substituted alkylamino, amide, substituted amide and carbamate; and R⁴ is hydrogen, alkyl, substituted alkyl, hydroxy, cyano or halogen;

or a pharmaceutically acceptable salt or stereoisomer thereof.

Representative compounds of the invention include the following

Ethyl 3-(3-(pyrrolo[1,2-f][1,2,4]triazin-4-ylamino)-1H-pyrazol-5-ylthio)benzoate;

3-(3-(Pyrrolo[1,2-f][1,2,4]triazin-4-ylamino)-1H-pyrazol-5-ylthio)benzoic acid;

N-(1-(Phenylsulfonyl)azetidin-3-yl)-3-(3-pyrrolo[1,2-f][1,2,4]triazin-4-ylamino-1H-pyrazol-5-ylthio)benzamide;

3-(3-(Pyrrolo[1,2-f][1,2,4]triazin-4-ylamino)-1H-pyrazol-5-ylthio)benzamide;

tert-Butyl 3-(3-(3-pyrrolo[1,2-f][1,2,4]triazin-4-ylamino)-1H-pyrazol-5-ylthio)benzamido)azetidine-1-carboxylate;

N-(Azetidin-3-yl)-3-(3-(pyrrolo[1,2-f][1,2,4]triazin-4-ylamino)-1H-pyrazol-5-ylthio)benzamide;

N-(1-(4-Fluorophenylsulfonyl)azeticin-3-yl)-3-(3-(pyrrolo[1,2-f][1,2,4]triazin-4-ylamino)-1H-pyrazol-5-ylthio)benzamide;

N-(2-(1H-Imidazol-4-yl)ethyl)-3-(3-(pyrrolo[1,2-f][1,2,4]triazin-4-ylamino)-1H-pyrazol-5-ylthio)benzamide;

N-(1-(Phenylsulfonyl)azetidin-3-yl)-3-(3-(pyridine-2-ylamino)-1H-pyrazol-5-ylthio)benzamide;

N-(1-(4-Fluorophenylsulfonyl)azetidin-3-yl)-3-(3-(pyridin-2-ylamino)-1H-pyrazol-5-ylthio)benzamide;

Ethyl 3-(3-(3-nitropyridin-2-ylamino)-1H-pyrazol-5-ylthio)benzoate; and

Ethyl 3-(3-(pyrrolo[1,2-f][1,2,4]triazin-4-ylamino)-1H-pyrazol-5-yloxy)benzoate;

or pharmaceutically acceptable salts thereof.

The following are definitions of terms that may be used in the specification. The initial definition provided for a group or term herein applies to that group or term throughout the specification individually or as part of another group, unless otherwise indicated.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. SO₂NH₂, substituted sulfonamido, nitro, cyano, carboxy, carbamyl, e.g. CONH₂, substituted carbamyl e.g. CONHalkyl, CONHaryl, CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl. Where noted above where the substituent is further substituted it will be with alkyl, alkoxy, aryl or arylalkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The terms "aryloxy", "arylamino", "arylalkylamino", "arylthio", "arylalkanoylamino", "arylsulfonyl", "arylalkoxy", "arylsulfinyl", "arylheteroaryl", "arylalkylthio", "arylcarbonyl", "arylalkenyl", or "arylalkylsulfonyl" refer to an aryl or substituted aryl bonded to an oxygen; an amino; an alkylamino; a thio; an alkanoylamino; a sulfonyl; an alkoxy; a sulfinyl; a heteroaryl or substituted heteroaryl; an alkylthio; a carbonyl; an alkenyl; or an alkylsulfonyl, respectively.

The term "arylsulfonylaminocarbonyl" refers to an arylsulfonyl bonded to an aminocarbonyl.

The terms "aryloxyalkyl", "aryloxycarbonyl" or "aryloxyaryl" refer to an aryloxy bonded to an alkyl or substituted alkyl; a carbonyl; or an aryl or substituted aryl, respectively.

The term "arylalkyl" refers to an alkyl or substituted alkyl in which at least one of the hydrogen atoms bonded to at least one of the carbon atoms is replaced with an aryl or substituted aryl. Typical arylalkyls include, but are not limited to, for example, benzyl, 2-phenylethan-1-yl, 2-phenylethen-1-yl, naphthylmethyl, 2-naphthylethan-1-yl, 2-naphthylethen-1-yl, naphthobenzyl, and 2-naphthophenylethan-1-yl.

The term "arylalkyloxy" refers to an arylalkyl bonded through an oxygen linkage (—O-arylalkyl).

The term "substituted aryl" refers to an aryl group substituted by, for example, one to four substituents such as alkyl, substituted alkyl, alkenyl, substituted alkenyl, alkynyl, substituted alkynyl, aryl, substituted aryl, arylalkyl, halo, trifluoromethoxy, trifluoromethyl, hydroxy, alkoxy, alkanoyl, alkanoyloxy, aryloxy, arylalkyloxy, amino, alkylamino, arylamino, arylalkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or arylalkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclyl, e.g. imidazolyl, furyl, thienyl, thiazolyl, pyrrolidyl, pyridyl, pyrimidyl and the like.

An "alkylidene" group refers to an alkylene group consisting of at least two carbon atoms and at least one carbon-carbon double bond.

The term "cycloalkyl" refers to an optionally substituted, saturated cyclic hydrocarbon ring systems, preferably containing 1 to 3 rings and 3 to 7 carbons per ring which may be further fused with an unsaturated $C_3$-$C_7$ carbocylic ring. Exemplary groups include cyclopropyl, cyclobutyl, cyclopentyl, cyclohexyl, cycloheptyl, cycloctyl, cyclodecyl, cyclododecyl, and adamantyl. Exemplary substituents include one or more alkyl groups as described above, or one or more groups described above as alkyl substituents.

The term "bicycloalkyl" means a bi-cyclic hydrocarbon ring system having from 8 to 14 carbon atoms and at least one saturated cyclic alkyl ring. Representative ($C_8$-$C_{14}$)bicycloalkyls include -indanyl, -1,2,3,4-tetrahydronaphthyl, -5,6,7,8-tetrahydronaphthyl, -perhydronaphthyl and the like.

The terms "heterocycle", "heterocyclic" and "heterocyclyl" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, homopiperazinyl, 2-oxohomopiperazinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, 1,3-benzodioxolyl, dihydrobenzofuryl, dihydrobenzothienyl, dihydrobenzothiopyranyl, dihydrobenzothiopyranyl sulfone, dihydrobenzopyranyl, indolinyl, indazolyl, isochromanyl, isoindolinyl, naphthyridinyl, phthalazinyl, piperonyl, purinyl, pyridopyridyl, pyrrolotriazinyl, quinazolinyl, tetrahydroquinolinyl, thienofuryl, thienopyridyl, thienothienyl, and the like.

Exemplary substituents include one or more alkyl or arylalkyl groups as described above or one or more groups described above as alkyl substituents.

Also included are smaller heterocyclyls, such as, epoxides and aziridines.

The term "heterocycloalkyl" refers to a heterocyclyl bonded to an alkyl or substituted alkyl group.

The term "carbocyclic ring" or "carbocyclyl" refers to stable, saturated, partially saturated or unsaturated, mono or bicyclic hydrocarbon rings that contain 3-12 atoms. Particularly, this includes a monocyclic ring containing 5 or 6 atoms or a bicyclic ring containing 9 or 10 atoms. Suitable values include cyclopropyl, cyclobutyl, cyclopentyl, cyclohexyl, cycloheptyl, dihydroindenyl and tetrahydronaphthyl. The term "optionally substituted" as it refers to "carbocyclic ring" or "carbocyclyl" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heteroatoms" shall include oxygen, sulfur and nitrogen.

The term "alkylsulfone" refers to $-R^kS(=O)_2R^k$, wherein $R^k$ is an alkyl or substituted alkyl.

The term "oxo" refers to the divalent radical $=O$.

The term "carbamate" refers to the group $-OC(=O)NH_2$.

The term "amide" refers to the group $-C(=O)NH_2$.

The term "sulfonamide" refers to the group $-SO_2NH_2$.

The terms "substituted amide", "substituted sulfonamide", or "substituted carbamate" refer to an amide, sulfonamide, or carbamate, respectively, having at least one hydrogen replaced with a group chosen from alkyl, substituted alkyl, alkenyl, substituted alkenyl, cycloalkyl, and substituted cycloalkyl.

A substituted amide, for example, refers to the group $-C(=O)NR^mR^n$ wherein $R^m$ and $R^n$ are independently selected from H, alkyl, substituted alkyl, alkenyl, substituted alkenyl, cycloalkyl, and substituted cycloalkyl, provided at least one of $R^m$ or $R^n$ is a substituted moiety.

A substituted sulfonamide, for example, refers to the group $-SO_2NR^oR^p$ wherein $R^o$ and $R^p$ are independently selected from alkyl, substituted alkyl, alkenyl, substituted alkenyl, cycloalkyl, and substituted cycloalkyl, provided at least one of $R^o$ or $R^p$ is a substituted moiety.

A substituted carbamate, for example, refers to the group $-OC(=O)NR^qR^r$ wherein $R^q$ and $R^r$ are independently selected from alkyl, substituted alkyl, alkenyl, substituted alkenyl, cycloalkyl, and substituted cycloalkyl, provided at least one of $R^q$ or $R^r$ is a substituted moiety.

The term "ureido" refers to the group $-NHC(=O)NH_2$.

The term "cyano" refers to the group $-CN$.

The terms "cycloalkylalkyl" or "cycloalkylalkoxy" refer to a cycloalkyl or substituted cycloalkyl bonded to an alkyl or substituted alkyl; or an alkoxy, respectively.

The term "nitro" refers to the group $-N(O)_2$.

The term "thio" refers to the group $-SH$.

The term "alkylthio" refers to the group $-SR^s$ where $R^s$ is an alkyl, substituted alkyl, cycloalkyl, or substituted cycloalkyl.

The term "thioalkyl" refers to the group $-R^tS$ where $R^t$ is an alkyl, substituted alkyl, cycloalkyl, or substituted cycloalkyl.

The term "alkylsulfonyl" refers to the group $-S(=O)_2R^u$ where $R^u$ is an alkyl, substituted alkyl, cycloalkyl, or substituted cycloalkyl.

The term "alkylsulfinyl" refers to the group $-S(=O)R^v$ where $R^v$ is an alkyl, substituted alkyl, cycloalkyl, or substituted cycloalkyl.

The term "carboxy" refers to the group $-C(=O)OH$.

The terms "carboxyalkoxy" or "alkoxycarbonylalkoxy" refer to a carboxy, or an alkoxycarbonyl, respectively, bonded to an alkoxy.

The term "alkoxycarbonyl" refers to the group $-C(=O)OR^w$ where $R^w$ is an alkyl, substituted alkyl, cycloalkyl, substituted cycloalkyl, aryl, substituted aryl, heteroaryl, or substituted heteroaryl.

The term "arylalkoxycarbonyl" refers to an aryl or substituted aryl bonded to an alkoxycarbonyl.

The terms "alkylcarbonyloxy" or "arylcarbonyloxy" refer to the group $-OC(=O)R^x$, where $R^x$ is an alkyl or substituted alkyl, or an aryl or substituted aryl, respectively.

The term "carbamoyl" refers to the groups $-OC(=O)NH_2$, $-OC(=O)NHR^x$, and/or $-OC(=O)NR^yR^z$, wherein $R^y$ and $R^z$ are independently selected from alkyl and substituted alkyl.

The term "carbonyl" refers to a $C(=O)$.

The terms "alkylcarbonyl", "aminocarbonyl", "alkylaminocarbonyl" "aminoalkylcarbonyl", or "arylaminocarbonyl" refer to an alkyl or substituted alkyl; an amino; an alkylamino or substituted alkylamino; an aminoalkyl or substituted aminoalkyl; or an arylamino, respectively, bonded to a carbonyl.

The terms "aminocarbonylaryl" or "aminocarbonylalkyl" refer to an aminocarbonyl bonded to an aryl or substituted aryl; or an alkyl or substituted alkyl, respectively.

The term "sulfonyl" refers to the group $S(=O)_2$.

The term "sulfinyl" refers to an $S(=O)$.

The term "carboxyalkyl" refers to an alkyl or substituted alkyl bonded to a carboxy.

The term "hydroxy" herein alone or as part of another group refers to $-OH$.

The compounds of formula I may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the formula I may also have prodrug forms. Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 112, pp. 309-396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, 8, 1-38 (1992).

It should further be understood that solvates (e.g., hydrates) of the compounds of formula I are also within the scope of the invention. Methods of solvation are generally known in the art.

According to a further aspect of the invention, there is provided the use of a compound of the formula I, or a pharmaceutically acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human being, in need of such treatment which comprises administering to said animal an effective amount of a compound of formula I or a pharmaceutically acceptable salt thereof as defined herein before.

The anti-proliferative treatment defined herein before may be applied as a sole therapy or may involve, in addition to a compound of the invention, one or more other substances and/or treatments. Such treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate.

The term "anti-cancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, Zoladex; matrix metalloproteinase inhibitors; VEGF inhibitors, such as anti-VEGF antibodies (Avastin™) and small molecules such as Brivanib, ZD6474 and SU6668; Vatalanib, BAY-43-9006, SU11248, CP-547632, and CEP-7055; HER 1 and HER 2 inhibitors including anti-HER2 antibodies (Herceptin); EGFR inhibitors including gefitinib, erlotinib, ABX-EGF, EMD72000, 11F8, and cetuximab; Eg5 inhibitors, such as SB-715992, SB-743921, and MKI-833; pan Her inhibitors, such as canertinib, EKB-569, CI-1033, AEE-788, XL-647, mAb 2C4, and GW-572016; Src inhibitors, e.g. Gleevec® and dasatinib; Casodex® (bicalutamide, Astra Zeneca), Tamoxifen; MEK-1 kinase inhibitors, MAPK kinase inhibitors, PI3 kinase inhibitors; PDGF inhibitors, such as imatinib; anti-angiogenic and antivascular agents which, by interrupting blood flow to solid tumors, render cancer cells quiescent by depriving them of nutrition; castration, which renders androgen dependent carcinomas non-proliferative; inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, desoxyepothilone A, desoxyepothilone B, Ixabepilone, [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo [14.1.0]-heptadecane-5,9-dione, and derivatives thereof; CDK inhibitors, antiproliferative cell cycle inhibitors, epidophyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists (e.g. 6-thioguanine and 6-mercaptopurine; glutamine antagonists, e.g. DON (AT-125; d-oxo-norleucine); ribonucleotide reductase inhibitors; mTOR inhibitors; and haematopoietic growth factors.

Additional cytotoxic agents include, cyclophosphamide, doxorubicin, daunorubicin, mitoxanthrone, melphalan, hexamethyl melamine, thiotepa, cytarabin, idatrexate, trimetrexate, dacarbazine, L-asparaginase, bicalutamide, leuprolide, pyridobenzoindole derivatives, interferons, and interleukins.

In the field of medical oncology it is normal practice to use a combination of different forms of treatment to treat each patient with cancer. In medical oncology the other component(s) of such treatment in addition to the antiproliferative treatment defined herein before may be surgery, radiotherapy or chemotherapy. Such chemotherapy may cover three main categories of therapeutic agent:

(i) antiangiogenic agents that work by different mechanisms from those defined hereinbefore (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, exemestane), antihormones, antiprogestogens, antiandrogens (for example, flutamide, nilutamide, bicalutamide, cyproterone acetate), LHRH agonists and antagonists (for example, gosereline acetate, leuprolide), inhibitors of testosterone 5α-dihydroreductase (for example, finasteride), farnesyltransferase inhibitors, anti-invasion agents (for example, metalloproteinase inhibitors such as marimastat and inhibitors of urokinase plasminogen activator receptor function) and inhibitors of growth factor function, (such growth factors include for example, EGF, FGF, platelet derived growth factor and hepatocyte growth factor, such inhibitors include growth factor antibodies, growth factor receptor antibodies such as Avastin® (bevacizumab) and Erbitux® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates such as methotrexate, fluoropyrimidines such as 5-fluorouracil, purine and adenosine analogues, cytosine arabinoside); intercalating antitumour antibiotics (for example, anthracyclines such as doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide nitrosoureas, thiotepa; antimitotic agents (for example, vinca alkaloids like vincristine, vinorelbine, vinblastine and vinflunine) and taxoids such as Taxol® (paclitaxel), Taxotere® (docetaxel) and newer microbtubule agents such as epothilone analogs (ixabepilone), discodermolide analogs, and eleutherobin analogs; topoisomerase inhibitors (for example, epipodophyllotoxins such as etoposide and teniposide, amsacrine, topotecan, irinotecan); cell cycle inhibitors (for example, flavopyridols); biological response modifiers and proteasome inhibitors such as Velcade® (bortezomib).

As stated above, the formula I compounds of the invention are of interest for their antiproliferative effects. Such compounds of the invention are expected to be useful in a wide range of disease states including cancer, psoriasis, and rheumatoid arthritis.

More specifically, the compounds of formula I are useful in the treatment of a variety of cancers, including (but not limited to) the following:

carcinoma, including that of the prostate, pancreatic ductal adreno-carcinoma, breast, colon, lung, ovary, pancreas, and thyroid;

tumors of the central and peripheral nervous system, including neuroblastoma, glioblastoma, and medulloblastoma; and other tumors, including melanoma and multiple myeloma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, pulmonary fibrosis, arthritis, psoriasis, glomerulonephritis, restenosis following angioplasty or vascular surgery, hypertrophic scar formation and inflammatory bowel disease The compounds of formula I are especially useful in treatment of tumors having a high incidence of tyrosine kinase activity, such as breast, prostate, colorectal, brain, head and neck, thyroid, lung and pancreatic tumors. Additionally, the compounds of the invention may be useful in treatment of sarcomas and pediatric sarcomas. By the administration of a composition (or a combination) of the compounds of this invention, development of tumors in a mammalian host is reduced.

Compounds of formula I may also be useful in the treatment of other cancerous diseases (such as acute myelogenous leukemia) that may be associated with signal transduction pathways operating through kinases such as Flt-3 (Fine-like kinase-3), Tie-2, CDK2, VEGFR, FGFR and IGFR kinases.

The pharmaceutical compositions of the invention containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ Model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of formula I may also be administered sequentially with known anticancer or cytotoxic agents when a combination formulation is inappropriate. The invention is not limited in the sequence of administration; compounds of formula I may be administered either prior to or after administration of the known anticancer or cytotoxic agent(s).

If formulated as a fixed dose, a combination product can, for example, utilize a dosage of the compound of formula I within the dosage range described above and the dosage of another anti-cancer agent/treatment within the approved dosage range for such known anti-cancer agent/treatment. If a combination product is inappropriate, the compound of formula I and the other anti-cancer agent/treatment can, for example, be administered simultaneously or sequentially. If administered sequentially, the present invention is not limited to any particular sequence of administration. For example, compounds of formula I can be administered either prior to, or after, administration of the known anti-cancer agent or treatment.

The compounds may be administered in a dosage range of about 0.05 to 200 mg/kg/day, preferably less than 100 mg/kg/day, in a single dose or in 2 to 4 divided doses.

Biological Assays

A. CDK 2/Cyclin E Kinase Assay

The assays were performed in U-bottom 384-well plates. The final assay volume was 30 µl prepared from 15 µl additions of enzyme and substrates (fluoresceinated CDK2E substrate peptide and ATP) and test compounds in assay buffer (100 mM HEPES pH 7.4, 10 mM $MgCl_2$, 0.015% Brij35 and 4 mM DTT). The reaction was initiated by the combination of bacterially expressed, CDK2E with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 30 µM; FL-peptide, 1.5 µM; CDK2E, 0.2 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

B. FLT3

The assays were performed in U-bottom 384-well plates. The final assay volume was 30 µl prepared from 15 µl additions of enzyme and substrates (fluoresceinated FLT3 substrate peptide and ATP) and test compounds in assay buffer (100 mM HEPES pH 7.4, 10 mM $MgCl_2$, 0.015% Brij35 and 4 mM DTT). The reaction was initiated by the combination of FLT3 with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 200 µM; FL-peptide, 1.5 µM; FLT3, 4.5 nM and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

C. GSK3-β

The assays were performed in U-bottom 384-well plates. The final assay volume was 30 µl prepared from 15 µl additions of enzyme and substrates (fluoresceinated peptide FL-GSK substrate and ATP) and test compounds in assay buffer (100 mM HEPES pH 7.2, 10 mM $MgCl_2$, 0.015% Brij35, 25 mM β-glycerolphosphate and 4 mM DTT). The reaction was initiated by the combination of GSK3-β with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 30 µM; FL-GSK substrate, 1.5 µM; His-GSK3B, 2.4 nM; and DMSO, 1.6%.

D. IGF1-Receptor Tyrosine Kinase Assay

The assays were performed in U-bottom 384-well plates. The final assay volume was 30 µl prepared from 15 µl additions of enzyme and substrates (fluoresceinated IGF1R substrate peptide and ATP) and test compounds in assay buffer (100 mM HEPES pH 7.4, 10 mM $MnCl_2$, 0.015% Brij35 and 4 mM DTT). The reaction was initiated by the combination of IGF1-receptor with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 25 µM; FL-peptide, 1.5 µM; IGF1-Receptor, 14 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis Compounds described herein were tested in the above assay. The following results were obtained.

| Example # | IGF-1R IC50 (µM) |
| --- | --- |
| 3 | 0.0124 |
| 10 | 0.0151 |
| 5 | 0.295 |
| 8 | 3.191 |
| 4 | 4.468 |
| 1 | >25 |

E. Insulin Receptor Tyrosine Kinase Assay

The assays were performed in U-bottom 384-well plates. The final assay volume was 30 µl prepared from 15 µl additions of enzyme and substrates (fluoresceinated InsR substrate peptide and ATP) and test compounds in assay buffer (100 mM HEPES pH 7.4, 10 mM $MnCl_2$, 0.015% Brij35 and 4 mM DTT). The reaction was initiated by the combination of Insulin Receptor with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 25 µM; FL-peptide, 1.5 µM; Insulin Receptor, 14 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis

F. JAK2

The assays were performed in U-bottom 384-well plates. The final assay volume was 30 µl prepared from 15 µl additions of enzyme and substrates (fluoresceinated peptide FL-JAK2 substrate and ATP) and test compounds in assay buffer (100 mM HEPES pH 7.2, 10 mM $MgCl_2$, 0.015% Brij35, 25 mM β-glycerolphosphate and 4 mM DTT). The reaction was initiated by the combination of activated JAK2 with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 30 µM; FL-JAK2 peptide, 1.5 µM; His-CDK5/p25, 2.6 nM; and DMSO, 1.6%.

G. LCK Kinase Assay

The assays were performed in U-bottom 384-well plates. The final assay volume was 30 µl prepared from 15 µl additions of enzyme and substrates (fluoresceinated LCK substrate peptide and ATP) and test compounds in assay buffer (100 mM HEPES pH 7.4, 10 mM $MnCl_2$, 0.015% Brij35 and 4 mM DTT). The reaction was initiated by the combination of LCK with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 3 µM; FL-peptide, 1.5 µM; Lck, 1 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

H. MapKapK2

The assays were performed in U-bottom 384-well plates. The final assay volume was 30 µl prepared from 15 µl additions of enzyme and substrates (fluoresceinated MK2 substrate peptide and ATP) and test compounds in assay buffer (100 mM HEPES pH 7.4, 10 mM $MgCl_2$, 0.015% Brij35 and 4 mM DTT). The reaction was initiated by the combination of MapKapK2 with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 1 µM; FL-peptide, 1.5 µM; MapKapK2, 0.08 nM; Brij35, 0.015% and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

I. Met Kinase Assay

Kinase reactions consisted of 0.75 ng of baculovirus expressed GST-Met, 3 ug poly(Glu/Tyr) (Sigma), 0.12 µCi 33P γ-ATP, 1 µM ATP in 30 µl kinase buffer (20 mm TRIS-Cl, 5 mM $MnCl_2$, 0.1 mg/ml BSA, 0.5 mM DTT). Reactions were incubated for 1 h at 30° C. and stopped by the addition of cold trichloroacetic acid (TCA) to a final concentration 8%. TCA precipitates were collected onto GF/C unifilter plates using a Filtermate universal harvester and the filters were quantitated using a TopCount 96-well liquid scintillation counter. Dose response curves were generated to determine the concentration required to inhibit 50% of kinase activity ($IC_{50}$). Compounds were dissolved at 10 mM in dimethylsulfoxide (DMSO) and evaluated at seven concentrations, each in triplicate.

J. p38alpha Assay

The assays were performed in U-bottom 384-well plates. The final assay volume was 30 µl prepared from 15 µl additions of enzyme and substrates (fluoresceinated P38a substrate peptide and ATP) and test compounds in assay buffer (100 mM HEPES pH 7.2, 10 mM $MgCl_2$, 0.015% Brij35 and 4 mM DTT). The reaction was initiated by the combination of activated p38alpha with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 20 µM; FL-peptide, 1.5 µM; p38alpha, 6 nM; and DMSO, 1.6%.

K. p38beta Assay

The assays were performed in U-bottom 384-well plates. The final assay volume was 30 µl prepared from 15 µl additions of enzyme and substrates (fluoresceinated P38b substrate peptide and ATP) and test compounds in assay buffer (100 mM HEPES pH 7.2, 10 mM $MgCl_2$, 0.015% Brij35 and 4 mM DTT). The reaction was initiated by the combination of activated p38beta with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 20 µM; FL-peptide, 1.5 µM; p38beta, 1 nM; and DMSO, 1.6%.

L. Protein Kinase A

The assays were performed in U-bottom 384-well plates. The final assay volume was 30 µl prepared from 15 µl additions of enzyme and substrates (fluoresceinated PKA substrate peptide and ATP) and test compounds in assay buffer (100 mM HEPES pH 7.4, 10 mM $MgCl_2$, 0.015% Brij35 and 4 mM DTT). The reaction was initiated by the combination of Protein kinase A with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 20 µM; FL-peptide, 1.5 µM, Protein kinase A 1 nM, and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

M. Protein Kinase C-alpha

The assays were performed in U-bottom 384-well plates. The final assay volume was 30 µl prepared from 15 µl additions of enzyme and substrates (fluoresceinated PKCa substrate peptide and ATP) and test compounds in assay buffer (100 mM HEPES pH 7.4, 10 mM $MgCl_2$, 0.015% Brij35 and 4 mM DTT). The reaction was initiated by the combination of Protein kinase C-alpha with lipids, substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 1 µM; FL-peptide, 1.5 µM; Protein kinase C-alpha, 1 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

N. TrkA Kinase Assay

Kinase reactions consisted of 0.12 ng of baculovirus expressed His-TrkA, 3 ug poly(Glu/Tyr) (Sigma), 0.24 µCi 33P γ-ATP, 30 µM ATP in 30 µl kinase buffer (20 mm MOPS, 10 mM $MgCl_2$, 1 mM EDTA, 0.015% Brij-35, 0.1 mg/ml BSA, 0.0025% Beta-Mercaptoethanol). Reactions were incubated for 1 h at 30° C. and stopped by the addition of cold trichloroacetic acid (TCA) to a final concentration 8%. TCA precipitates were collected onto GF/C unifilter plates using a Filtermate universal harvester and the filters were quantitated using a TopCount 96-well liquid scintillation counter. Dose response curves were generated to determine the concentration required to inhibit 50% of kinase activity ($IC_{50}$). Compounds were dissolved at 10 mM in dimethylsulfoxide (DMSO) and evaluated at seven concentrations, each in triplicate.

O. TrkB Kinase Assay

Kinase reactions consisted of 0.75 ng of baculovirus expressed His-TrkB, 3 ug poly(Glu/Tyr) (Sigma), 0.24 µCi 33P γ-ATP, 30 µM ATP in 30 µl kinase buffer (20 mm MOPS, 10 mM $MgCl_2$, 1 mM EDTA, 0.015% Brij-35, 0.1 mg/ml BSA, 0.0025% Beta-Mercaptoethanol). Reactions were incubated for 1 h at 30° C. and stopped by the addition of cold trichloroacetic acid (TCA) to a final concentration 8%. TCA precipitates were collected onto GF/C unifilter plates using a Filtermate universal harvester and the filters were quantitated using a TopCount 96-well liquid scintillation counter. Dose response curves were generated to determine the concentration required to inhibit 50% of kinase activity ($IC_{50}$). Compounds were dissolved at 10 mM in dimethylsulfoxide (DMSO) and evaluated at seven concentrations, each in triplicate.

Methods of Preparation

Compounds of formula I may generally be prepared according to Schemes 1 and 2 and the knowledge of one skilled in the art.

3,3-Dichloroacrylonitrile IV [described in S. Yodoyama, T. Sato, K. Kimura, N. Furutachi, O. Takahashi. EP 0271063] can be used as starting material for the synthesis of both the S-and O-linked intermediates VI. Compound IV may be treated with various 3-mercaptobenzoic acids, 3-hydroxybenzoic acids or 4-mercaptopicolinic acids in presence of a base such as sodium or potassium hydroxide and the like in a solvent such as tetrahydrofuran to give intermediates of type V. Subsequent heating with hydrazine will yield to the corresponding aminopyrrazoles which may then be esterified in presence of an acid such as sulfuric acid, hydrochloric acid and the like in ethanol or methanol to give the intermediates VI.

Substitution of the aminopyrrazole to the intermediates VII may be accomplished by heating various substituted haloaryls or haloheteroaryls in presence of an acid such as hydrobromic acid in isopropanol. Microwave heating may be advantageously used to accelerate the reactions. Alternatively, the reaction may proceed in presence of a base such as diisopropylethylamine or triethylamine and the like in refluxing isopropanol.

SCHEME 1

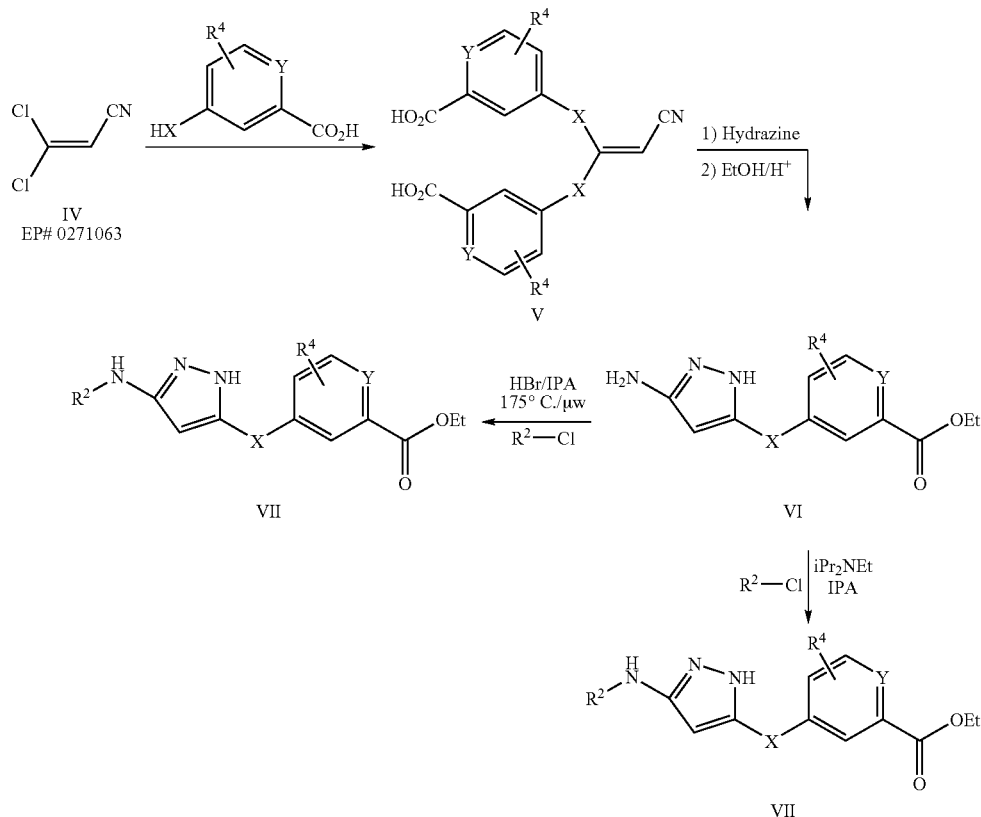

Intermediates of type VII may then be saponified to the corresponding acids in the conditions known by those skilled-in-the-art. Coupling with the desired amines was then performed in presence of EDAC (1-[3-dimethylaminopropyl]-3-ethyl carbodiimide hydrochloride), hydroxybenzotriazole and a base such as diisopropylethylamine, triethylamine and the like to afford the compounds of type I, II or III. It is understood that any other coupling methods known in the art may be also utilized to yield compounds I, II or III.

SCHEME 2

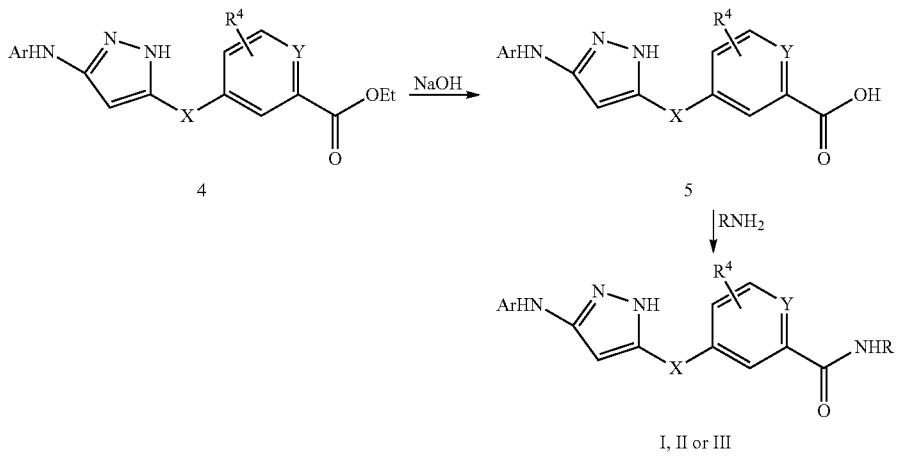

In addition, other compounds of formula I may be prepared using procedures generally known to those skilled in the art. In particular, the following examples provide additional methods for the preparation of the compounds of this invention.

EXAMPLES

The invention will now be further described by the following working example(s), which are preferred embodiments of the invention. All temperatures are in degrees Celsius (° C.) unless otherwise indicated. All reactions were carried out with continuous magnetic stirring under an atmosphere of argon. All evaporations and concentrations were carried out on a rotary evaporator under reduced pressure. Commercial reagents were used as received without additional purification. Solvents were commercial anhydrous grades and were used without further drying or purification. Flash chromatography was performed using silica gel (EMerck Kieselgel 60, 0.040-0.060 mm).

The following abbreviations may be employed herein: CDCl₃: deuterated Chloroform, DMSOd₆: deuterated dimethyl sulfoxide, CD₃OD: deuterated methanol NH₄OAc: ammonium acetate, TFA: trifluoroacetic acid, min.: minute(s), h or hr(s): hour(s), mL: milliliter, μL: microliter, g: gram(s), mg: milligram(s), mol.: moles, mmol: millimole(s), nM: nanometer, ret. time.: HPLC retention time (minutes), sat.: saturated, aq.: aqueous, conc.: concentrated, HPLC: high performance liquid chromatography, Prep HPLC: preparative reverse phase HPLC, LC/MS: high performance liquid chromatography/mass spectrometry, HRMS: high resolution mass spectrometry, NMR: nuclear magnetic resonance, MeCN: acetonitrile.

Analytical HPLCs were obtained under the following conditions:

A: Primesphere C18, 4.6×30 mm, 2 min. gradient, 0% B to 100% B, Solvent A: 10% MeCN-90% water-0.1% TFA, Solvent B: 90% MeCN-10% water-0.1% TFA, 4 mL/min., 220 nM.

B: ZorbaxSB C18, 4.6×75 mm, 8 min. gradient, 0% B to 100% B, Solvent A: 10% MeCN-90% water-0.1% TFA, Solvent B: 90% MeCN-10% water-0.1% TFA, 2.5 mL/min., 220 nM.

C: Primesphere C18, 4.6×30 mm, 2 min. gradient, 0% B to 100% B, Solvent A: 10% MeCN-90% water-0.1% TFA, Solvent B: 90% MeCN-10% water-0.1% TFA, 4 mL/min., 254 nM.

The NMR spectra were taken on a Bruker 400 mHz. These examples are illustrative rather than limiting and it is to be understood that there may be other embodiments that fall within the spirit and scope of the invention as defined by the claims appended hereto.

Synthesis of Intermediates

A. Preparation of 3,3-dichloroacrylonitrile

The synthesis of this intermediate was performed according to a known literature procedure that was modified [S. Yodoyama, T. Sato, K. Kimura, N. Furutachi, O. Takahashi. EP 0271063].

1) Preparation of 2,2,2-trichloro-1-cyanoethyl acetate

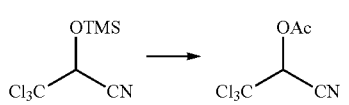

Zinc iodide (3.0 g, 9.7 mmol) was added to a solution of chloral (15.0 g, 101.7 mmol) in dichloromethane (100 mL) and this was stirred for 15 minutes. The reaction was then cooled to ~10° C. and trimethylsilylcyanide (13.0 mL, 97.0 mmol) was added dropwise over 30 minutes. The mixture was then stirred at room temperature for 3.5 hours. The solid was removed by filtration and the filtrate was concentrated to dryness to give a liquid (~25 g) which was used as such for the next reaction.

This liquid was dissolved in dichloromethane (15 mL) and acetic anhydride (60 mL) and the mixture was refluxed for 24 hours. After cooling down to room temperature, the reaction was filtered to remove a solid and the filtrate was concentrated. The residue was purified by silica gel column chromatography (30% hexane in dichloromethane) to give the title material (18.2 g, 87%) as an oil. ¹H NMR 400 MHz CDCl₃ δ (ppm): 2.32 (3 H, s), 6.11 (1 H, s).

2) Preparation of 3,3-dichloroacrylonitrile

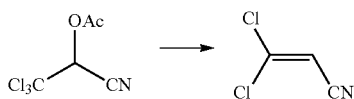

A solution of 2,2,2-trichloro-1-cyanoethyl acetate (18.2 g, 84.0 mmol) in tetrahydrofuran (50 mL) was refluxed and zinc dust (6.05 g, 92.5 mmol) was slowly added to this boiling solution. The reaction was stirred at reflux for 3 hours. The reaction was then concentrated and the residue was purified on silica gel column chromatography (30% hexane in dichloromethane) to give the title material (8.30 g, 81%) as an oil. ¹H NMR 400 MHz CDCl₃ δ (ppm): 5.90 (1H, s).

B. Preparation of ethyl 3-(3-amino-1H-pyrazol-5-ylthio)benzoate

1) Preparation of 3,3-bis-(3-sulfanyl-benzoic acid)acrylonitrile

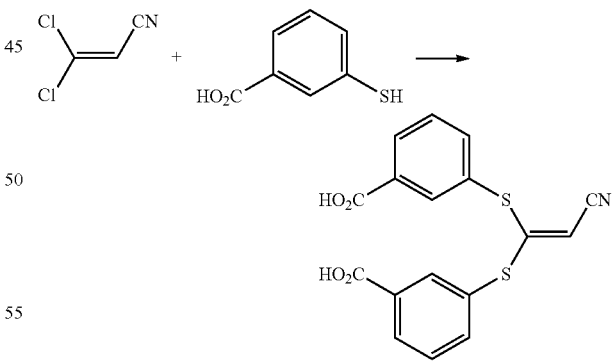

To a stirred solution of 3-mercaptobenzoic acid (5.3 g, 34.4 mmol) and sodium hydroxide (2.75 g, 68.9 mmol) in water (100 mL) at 0° C., was added a solution of 3,3-dichloroacrylonitrile (2.0 g, 16.4 mmol) in tetrahydrofuran (10 mL). The reaction was allowed to reach room temperature and stirred overnight. The mixture was then acidified with conc. hydrochloric acid, extracted with ethyl acetate, dried over anhydrous magnesium sulphate, filtered and concentrated. The residue was crystallized in ethyl acetate to give the title material (3.2 g, 55%) as a solid along with the impure material (3.0 g). ¹H NMR 400 MHz DMSO-d₆ δ (ppm): 5.75 (1H, s), 7.52-7.63 (3H, m), 7.67-7.72 (1H, m), 7.74-7.80 (1H, m), 7.82-7.88 (1H, m), 7.96-8.02 (2H, m), 13.28 (2H, s).

2) Preparation of ethyl 3-(3-amino-1H-pyrazol-5-ylthio)benzoate

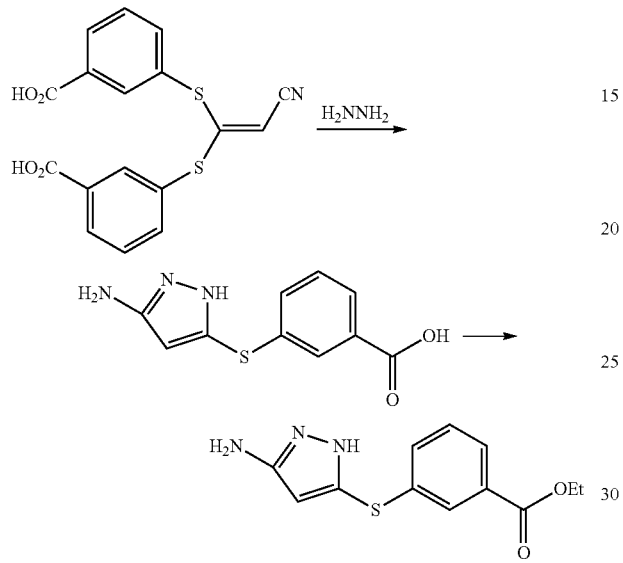

3,3-Bis-(3-sulfanyl-benzoic acid)acrylonitrile (0.5 g, 1.4 mmol) was refluxed in hydrazine hydrate (4 mL) for ~0.5 hours. The reaction was concentrated to give a syrup which was used as such for the next reaction. The syrup was dissolved in ethanol (10 mL) and treated with conc. sulfuric acid (1 mL). This mixture was refluxed overnight, then filtered. The filtrate was concentrated, diluted with ethyl acetate and tetrahydrofuran, washed with sat. aq. sodium bicarbonate, dried over anhydrous magnesium sulfate, filtered and concentrated. The residue was purified on Biotage (50% hexane in ethyl acetate to 100% ethyl acetate) to give the title material (0.119 g, 32%) as an oil. ¹H NMR 400 MHz DMSO-d₆ δ (ppm): 1.30 (3H, t, J=7.07 Hz), 4.29 (2H, q, J=7.07 Hz), 5.23 (2H, s), 5.37 (1H, s), 7.38-7.53 (2H, m), 7.66-7.79 (2H, m), 11.96 (1H, s).

C. Preparation of ethyl 3-(3-amino-1H-pyrazol-5-yloxy)benzoate

1) Preparation of 3,3-bis-(3-oxy-benzoic acid)acrylonitrile

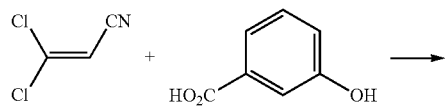

-continued

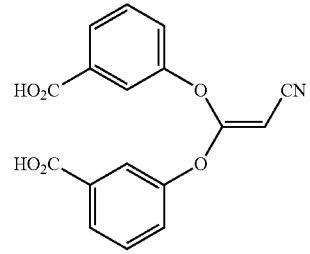

A solution of 3,3-dichloroacrylonitrile (1.0 g, 8.2 mmol) in tetrahydrofuran (5 mL) was slowly added to a solution of 3-hydroxy-benzoic acid (2.38 g, 17.2 mmol), sodium hydroxide (1.35 g, 33.6 mmol) in water (75 mL). This mixture was stirred at room temperature for 2 hours and then heated at 75° C. overnight. The reaction was then cooled down and acidified with conc. hydrochloric acid and extracted with ethyl acetate. The combined organic layers were dried over anhydrous magnesium sulphate, filtered and concentrated to give the title material as a solid which will be used as is for the next reaction. A small quantity (60 mgs) was purified by Prep HPLC (ammonium acetate/water/acetonitrile). ¹H NMR 400 MHz DMSO-d₆ δ (ppm): 4.30 (1H, s), 7.20-7.30 (1H, m), 7.32-7.38 (1H, m), 7.39-7.48 (2H, m), 7.62 (1H, s), 7.69-7.86 (3H, m), 7.90 (2H, br s). LCMS (⁻ESI, M−H⁺) m/z 324.

2) Preparation of ethyl 3-(3-amino-1H-pyrazol-5-yloxy)benzoate

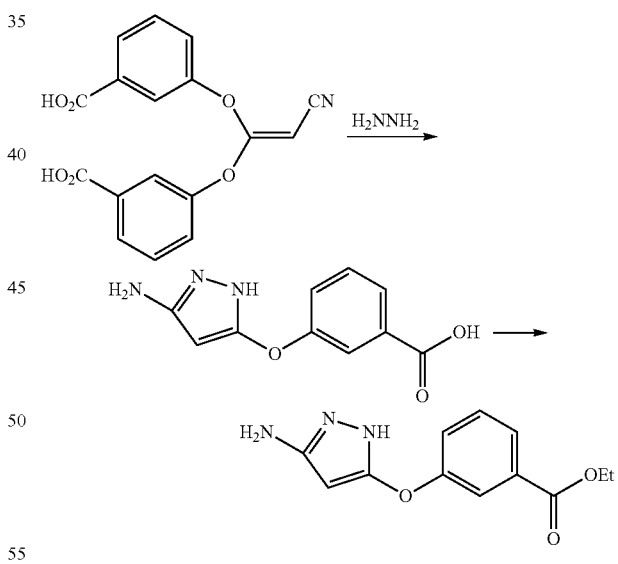

A mixture of 3,3-bis-(3-oxy-benzoic acid)acrylonitrile (~2.67 g, ~8.2 mmol, crude) and hydrazine hydrate (8 mL) was heated at 50° C. for 30 minutes. The mixture was then concentrated to dryness and the residue was dissolved in ethanol and sulphuric acid (10 mL). This reaction was stirred at a gentle reflux for 2 hours and was then concentrated. The residue was diluted in ethyl acetate, washed with sat. sodium carbonate, dried over anhydrous magnesium sulphate, filtered and concentrated. The residue was purified on Biotage (50-100% hexane in ethyl acetate) to give the title material (0.264 g, 13%) as a gum. ¹H NMR 400 MHz CDCl₃ δ (ppm):

1.40 (3H, t, J=7.20 Hz), 4.38 (2H, q, J=7.07 Hz), 5.11 (1H, s), 7.32-7.38 (1H, m), 7.41 (1H, t, J=7.71 Hz), 7.78-7.85 (2H, m). HPLC (220 nm): 91%. LCMS (⁺ESI, M+H⁺) m/z 248. (⁻ESI, M−H⁺) m/z 246.

D. Preparation of 4-chloropyrrolo[1,2-f][1,2,4]triazine

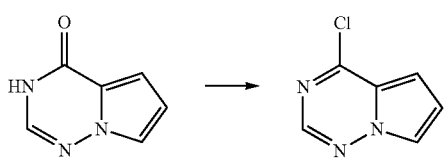

To a solution of pyrrolo[1,2-f][1,2,4]triazine-4(3H)-one [prepared as described in S. A. Patil, B. A. Otter and R. S. Klein, *J. Het. Chem.*, 31, 781-786 (1994)] (450 mgs, 3.3 mmol) in toluene (12 mL) was added diisopropylethylamine (0.6 mL, 3.3 mmol) and phosphorus oxychloride (0.80 mL, 4.95 mmol). The mixture was heated at 120° C. overnight then cooled to room temperature, poured into sat. sodium bicarbonate/ice (1:1) and stirred for 30 minutes. This was extracted with toluene (1×100 mL) and the organic phase was dried over anhydrous magnesium sulfate, filtered and concentrated. The residue was purified on Biotage (dichloromethane) to give the title material (405 mgs, 80%). ¹H NMR 400 MHz CD₃OD δ (ppm): 7.03 (2H, s), 8.00 (1H, br s), 8.22 (1H, s).

E. Preparation of tert-butyl 1-(phenylsulfonyl)azetidin-3-ylcarbamate

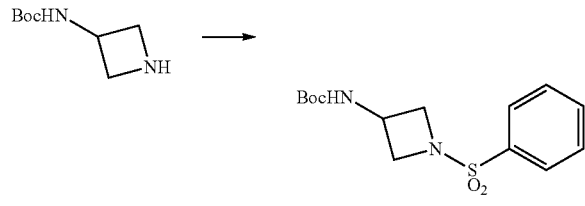

To a stirred suspension of tert-butyl azetidin-3-ylcarbamate (4.61 g, contaminated with diphenylmethane 1:1, ~13.39 mmoles) in dichloromethane (150 mL), was added triethylamine (3.73 mL, 26.77 mmoles) and benzenesulfonyl chloride (2.57 mL, 20.08 mmoles). The reaction was stirred at room temperature for ~4 hours and became a solution. Sat. ammonium chloride was added to the mixture and the aqueous phase was extracted with dichloromethane (3×). The combined organic layers were dried over anhydrous magnesium sulphate, filtered and concentrated. The residue was precipitated from dichloromethane/hexanes 1:1 to give the title material (1.073 g, ~26%) as a solid. The mother liquor was concentrated and the residue was purified on Biotage (0 to 20% acetonitrile in dichloromethane) to afford the title material (2.46 g, ~58%). ¹H NMR 400 MHz CDCl₃ δ (ppm):

1.42 (9H, s), 3.60 (2H, br s), 4.06 (2H, dd, J=8.7 and 7.7 Hz), 4.35 (1H, br s), 4.70 (1H, br s), 7.60-7.64 (2H, m), 7.68-7.72 (1H, m), 7.86-7.88 (2H, m).

F. Preparation of tert-butyl 1-(4-fluorophenylsulfonyl)azetidin-3-ylcarbamate

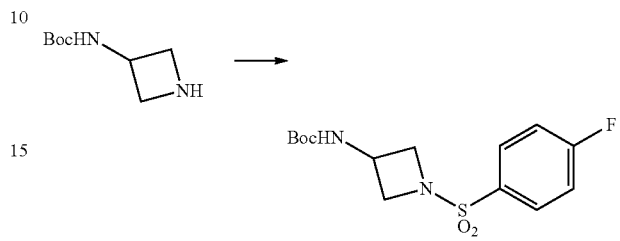

The synthesis has been carried out as described in Example E for the preparation of tert-butyl 1-(phenylsulfonyl)azetidin-3-ylcarbamate. ¹H NMR 400 MHz CDCl₃ δ (ppm): 1.43 (9H, s), 3.62 (2H, br t, J=7.3 Hz), 4.05 (2H, dd, J=8.6 and 7.7 Hz), 4.36 (1H, br s), 4.74 (1H, br s), 7.26-7.32 (2H, m), 7.87-7.91 (2H, m).

Example 1

Ethyl 3-(3-(pyrrolo[1,2-f][1,2,4]triazin-4-ylamino)-1H-pyrazol-5-ylthio)benzoate

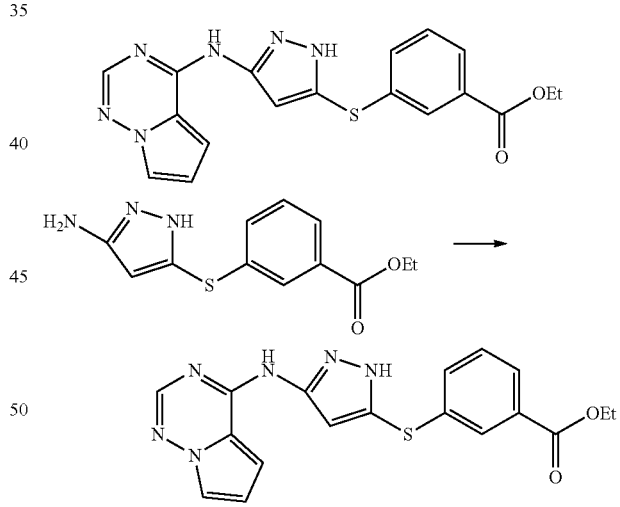

A mixture of 4-chloropyrrolo[1,2-f][1,2,4]triazine (100 mgs, 0.65 mmol), ethyl 3-(3-amino-1H-pyrazol-5-ylthio)benzoate (171 mgs, 0.65 mmol), diisopropylethylamine (347 μL, 1.95 mmol) in isopropanol (2 mL) was heated at 95° C. in a sealed tube for 3 days. The reaction was cooled to room temperature and filtered. The filtrate was purified on preparative HPLC (MeCN/H₂O/0.1% TFA) to afford the title material (142 mgs, 44%) as a solid. ¹H NMR 400 MHz DMSO-d₆ δ (ppm): 1.29 (3H, t, J=7.20 Hz), 4.30 (2H, q, J=7.07 Hz), 6.74 (1H, dd, J=4.29, 2.53 Hz), 7.00 (1H, s), 7.24 (1H, s), 7.52 (2H, d, J=5.05 Hz), 7.72-7.87 (3H, m), 8.03 (1H, s), 10.89

(1H, s). HPLC ret. time (Condition B): 4.797 min; 86%. LCMS (+ESI, M+H+) m/z 381.

Example 2

3-(3-(Pyrrolo[1,2-f][1,2,4]triazin-4-ylamino)-1H-pyrazol-5-ylthio)benzoic acid

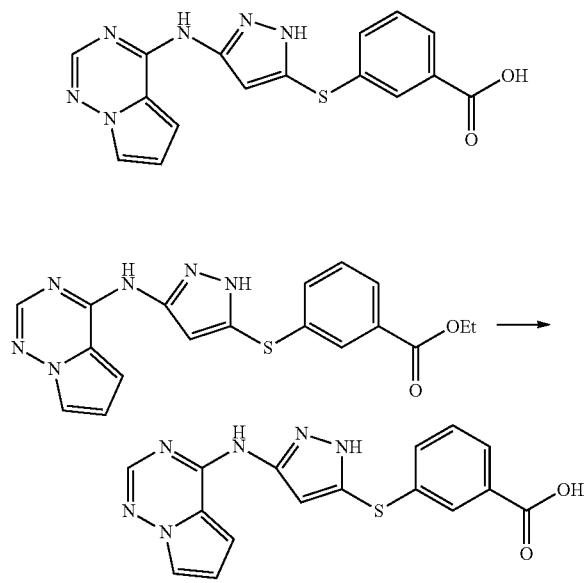

To a solution of ethyl 3-(3-(pyrrolo[1,2-f][1,2,4]triazin-4-ylamino)-1H-pyrazol-5-ylthio)benzoate (130 mgs, 0.26 mmol) in ethanol (5 mL) was added 20% aq. sodium hydroxide (3 mL) and the reaction was stirred overnight at room temperature. The reaction was then concentrated to dryness and the gummy residue was dissolved in N,N-dimethylformamide and water and acidified with acetic acid. The resulting precipitate was filtered and vacuum dried to give the title material (87 mgs, 95%) as a solid. $^1$H NMR 400 MHz DMSO-d$_6$ δ (ppm): 6.73 (1H, s), 7.25 (2H, s), 7.44-7.55 (3H, m), 7.67-7.84 (3H, m), 8.02 (1H, s), 10.82 (1H, s), 13.29 (1H, s). HPLC ret. time (Condition C): 1.320 min; 98%. LCMS (+ESI, M+H+) m/z 353.

Example 3

N-(1-(Phenylsulfonyl)azetidin-3-yl)-3-(3-pyrrolo[1,2-f][1,2,4]triazin-4-ylamino-1H-pyrazol-5-ylthio)benzamide

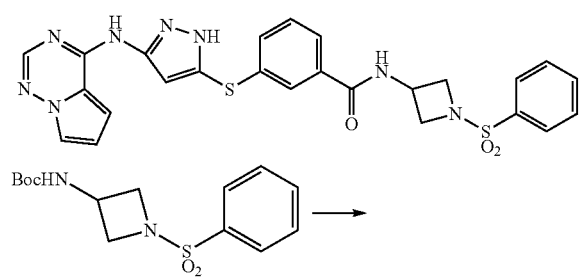

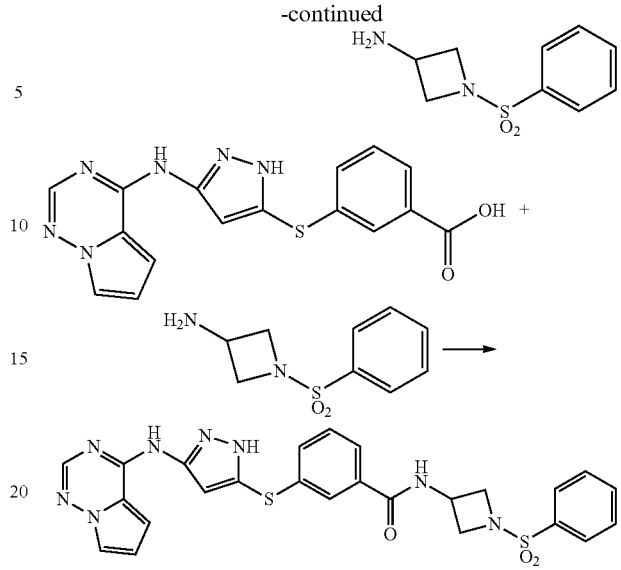

A stirred solution of tert-butyl 1-(phenylsulfonyl)azetidin-3-ylcarbamate (34 mgs, 0.109 mmol) in dichloromethane (5 mL) was treated with trifluoroacetic acid (1 mL) at room temperature. After 15 minutes, the reaction was concentrated to dryness and the residue was dissolved in N-methylpyrrolidone (1 mL). To this mixture was added 3-(3-(pyrrolo[1,2-f][1,2,4]triazin-4-ylamino)-1H-pyrazol-5-ylthio)benzoic acid (35 mgs, 0.099 mmol), N-(3-dimethylaminopropyl)-N'-ethylcarbodiimide hydrochloride (25 mgs, 0.129 mmol), hydroxybenzotriazole (13 mgs, 0.099 mmol) and diisopropylethylamine (0.088 mL, 0.495 mmol) and the reaction was stirred at room temperature for ~4 hours. N-(3-dimethylaminopropyl)-N'-ethylcarbodiimide hydrochloride (10 mgs, 0.05 mmol) was added again and the reaction was stirred for one more hour. The mixture was then neutralized with conc. hydrochloric acid and purified on preparative HPLC (MeCN/H$_2$O/5 mM NH$_4$OAc) to afford the title material (35 mgs, 65%) as a solid. $^1$H NMR 400 MHz DMSO-d$_6$ δ (ppm): 3.73 (2H, dd, J=8.46, 6.44 Hz), 3.99 (2H, t, J=8.21 Hz), 4.33-4.47 (1H, m), 6.72 (1H, dd, J=4.04, 2.78 Hz), 7.19-7.28 (1H, m), 7.31-7.38 (1H, m), 7.43 (1H, t, J=7.83 Hz), 7.57-7.81 (7H, m), 7.81-7.89 (2H, m), 8.00 (1H, s), 8.96 (1H, d, J=6.06 Hz), 10.82 (1H, s), 13.32 (1H, s). HPLC ret. time (Condition B): 4.553 min.; 94%. LCMS (+ESI, M+H+) m/z 547; (−ESI, M−H+) m/z 545, HRMS: calc. 547.1335, found 547.1328.

Example 4

3-(3-(Pyrrolo[1,2-f][1,2,4]triazin-4-ylamino)-1H-pyrazol-5-ylthio)benzamide

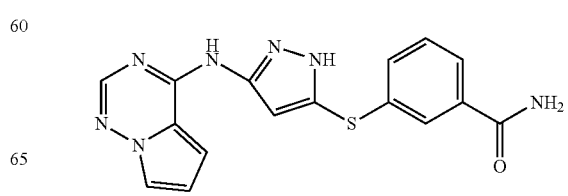

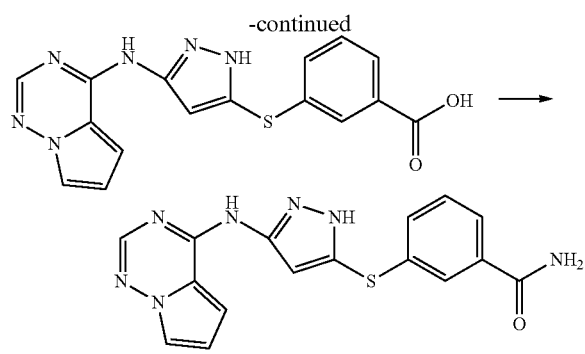
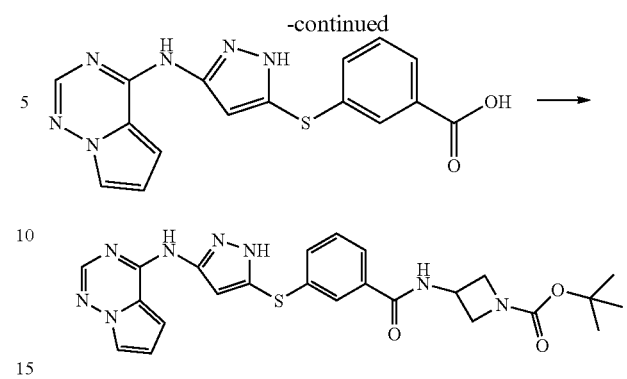

ylthio)benzoic acid (0.090 g, 0.25 mmol), 2-chloro-1-methylpyridinium iodide (0.078 g, 0.30 mmol), ammonium chloride (0.067 g, 1.25 mmol) and diisopropylethylamine (0.135 mL, 0.75 mmol) in N-methylpyrrolidone (4 mL) was stirred at room temperature for 30 minutes. The mixture was then purified on Prep HPLC (MeCN/H$_2$O/5 mM NH$_4$OAc) to afford the title material (0.054 g, 60%) as a solid. $^1$H NMR 400 MHz DMSO-d$_6$ δ (ppm): 6.65-6.77 (1H, m, J=2.02 Hz), 7.24 (2H, s), 7.31-7.54 (3H, m), 7.66-7.81 (3H, m), 7.94-8.10 (2H, m), 10.80 (1H, s), 13.31 (1H, s). HPLC ret. time (Condition B): 3.085 min.; 96%. LCMS ($^+$ESI, M+H$^+$) m/z 352, ($^-$ESI M−H$^+$) m/z 350, HRMS: calc. 352.0981, found 352.0996.

Example 5 tert-Butyl 3-(3-(3-pyrrolo[1,2-f][1,2,4]triazin-4-ylamino)-1H-pyrazol-5-ylthio)benzamido)azetidine-1-carboxylate

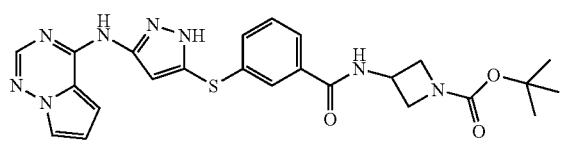

To a mixture of tert-butyl 3-aminoazetidine-1-carboxylate (0.048 g, 0.28 mmol) in N-methylpyrrolidone (3 mL) was added 3-(3-(pyrrolo[1,2-f][1,2,4]triazin-4-ylamino)-1H-pyrazol-5-ylthio)benzoic acid 0.090 g, 0.26 mmol), N-(3-dimethylaminopropyl)-N'-ethylcarbodiimide hydrochloride (0.073 g, 0.38 mmol), hydroxybenzotriazole (0.035 g, 0.26 mmol) and diisopropylethylamine (0.227 mL, 1.28 mmol) and the reaction was stirred at room temperature overnight. The mixture was then neutralized with conc. hydrochloric acid and purified on preparative HPLC (MeCN/H$_2$O/5 mM NH$_4$OAc) to afford the title material (0.069 g, 52%) as a solid. $^1$H NMR 400 MHz DMSO-d$_6$ δ (ppm): 1.39 (9H, s), 3.78-3.91 (2H, m), 4.03-4.19 (2H, m), 4.55-4.69 (1H, m), 6.68-6.77 (1H, m, J=1.77 Hz), 7.05-7.41 (3H, m), 7.47 (1H, t, J=7.83 Hz), 7.67-7.84 (3H, m), 8.01 (1H, s), 9.06 (1H, d, J=7.07 Hz), 10.80 (1H, s), 13.31 (1H, s). HPLC ret. time (Condition B): 4.577 min.; 98%. LCMS ($^+$ESI, M+H$^+$) m/z 507; ($^-$ESI M−H) m/z 505, HRMS: calc. 507.1927, found 507.1946.

Example 6

N-(Azetidin-3-yl)-3-(3-(pyrrolo[1,2-f][1,2,4]triazin-4-ylamino)-1H-pyrazol-5-ylthio)benzamide

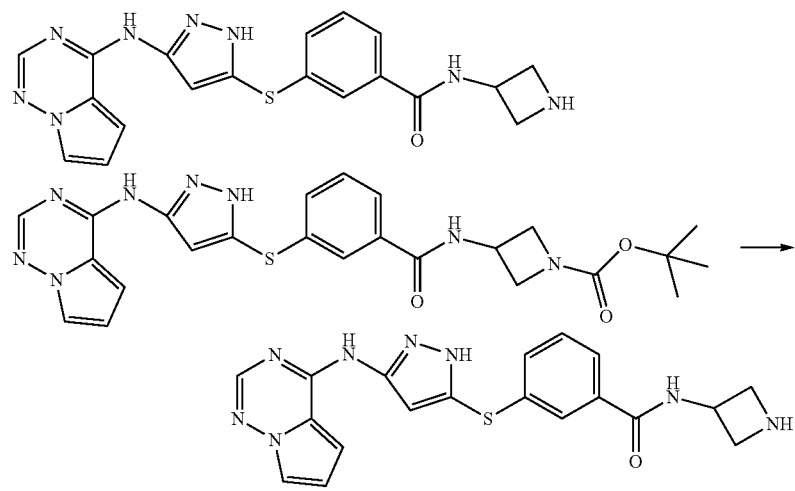

tert-Butyl 3-(3-(3-pyrrolo[1,2-f][1,2,4]triazin-4-ylamino)-1H-pyrazol-5-ylthio)benzamido)azetidine-1-carboxylate (0.040 g, 0.08 mmol) was dissolved in dichloromethane (10 mL) and treated with trifluoroacetic acid (4 mL) and the reaction was stirred at room temperature for 2 hours. The mixture was concentrated to dryness and the residue was purified on Prep HPLC (MeCN/H$_2$O/5 mM NH$_4$OAc) to give the title material (0.03 μg, 83%, acetic acid salt) as a solid. $^1$H NMR 400 MHz DMSO-d$_6$ δ (ppm): 1.89 (2H, s), 3.59-3.75 (4H, m), 4.60-4.76 (1H, m), 6.72 (1H, dd, J=4.42, 2.65 Hz), 6.97 (1H, s), 7.25 (1H, d, J=3.28 Hz), 7.32-7.39 (1H, m, J=8.84 Hz), 7.45 (1H, t, J=7.83 Hz), 7.65-7.79 (3H, m), 8.01 (1H, s), 9.02 (1H, d, J=6.82 Hz). HPLC ret. time (Condition B): 2.861 min.; 100%. LCMS ($^+$ESI, M+H$^+$) m/z 407. HRMS: calc. 407.1403, found 407.1386.

Example 7

N-(1-(4-Fluorophenylsulfonyl)azeticin-3-yl)-3-(3-(pyrrolo[1,2-f][1,2,4]triazin-4-ylamino)-1H-pyrazol-5-ylthio)benzamide

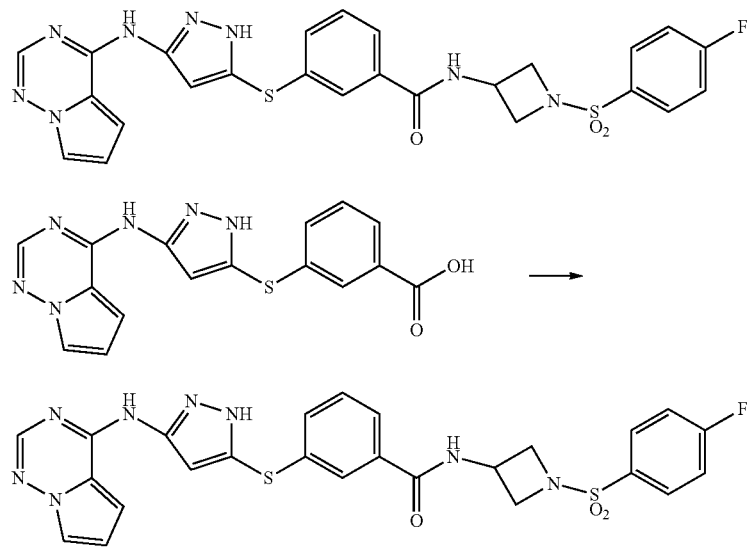

3-(3-(Pyrrolo[1,2-f][1,2,4]triazin-4-ylamino)-1H-pyrazol-5-ylthio)benzoic acid (0.090 g, 0.26 mmol) and tert-butyl 1-(4-fluoro-phenylsulfonyl)azetidin-3-ylcarbamate (0.101 g, 0.31 mmol) were treated as described in Example 3, except that the mixture was purified on Prep HPLC (MeCN/H$_2$O/ 0.1% TFA). This afforded the title material (0.084 g, 48%, trifluoroacetic acid salt) as a solid. $^1$H NMR 400 MHz DMSO-d$_6$ δ (ppm): 3.72 (2H, dd, J=8.46, 6.44 Hz), 4.00 (2H, t, J=8.08 Hz), 4.33-4.51 (1H, m), 6.73 (1H, dd, J=4.29, 2.53 Hz), 6.96 (1H, s), 7.22 (1H, s), 7.32-7.39 (1H, m), 7.44 (1H, t, J=7.71 Hz), 7.49-7.58 (2H, m), 7.61 (1H, d, J=7.83 Hz), 7.66 (1H, s), 7.75-7.80 (1H, m), 7.88-7.97 (2H, m), 8.02 (1H, s), 8.96 (1H, d, J=6.06 Hz), 10.86 (1H, s). HPLC ret. time (Condition B): 4.730 min.; 100%. LCMS ($^+$ESI, M+H$^+$) m/z 565. HRMS: calc. 565.1240, found 565.1224.

Example 8

N-(2-(1H-Imidazol-4-yl)ethyl)-3-(3-(pyrrolo[1,2-f][1,2,4]triazin-4-ylamino)-1H-pyrazol-5-ylthio)benzamide

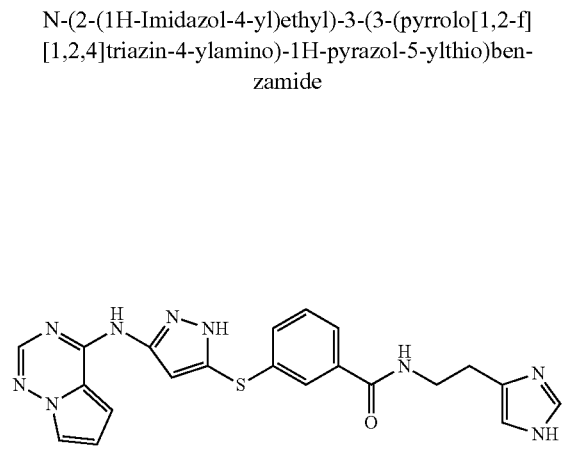

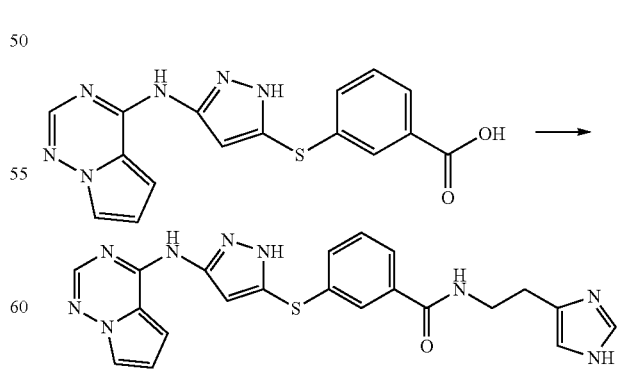

3-(3-(Pyrrolo[1,2-f][1,2,4]triazin-4-ylamino)-1H-pyrazol-5-ylthio)benzoic acid (0.090 g, 0.26 mmol) and 2-(1H-imidazol-4-yl)ethanamine bis hydrochloride salt (0.061 g, 0.33 mmol) were treated as described in Example 5 except that the mixture was purified on Prep HPLC (MeCN/H₂O/ 0.1% TFA). This afforded the title material (0.066 g, 45%, trifluoroacetic acid salt) as a solid. ¹H NMR 400 MHz DMSO-d₆ δ (ppm): 2.89 (2H, t, J=6.69 Hz), 3.54 (2H, q, J=6.57 Hz), 6.73 (1H, dd, J=4.29, 2.78 Hz), 6.99 (1H, s), 7.24 (1H, s), 7.32-7.39 (1H, m), 7.41-7.51 (2H, m), 7.65 (1H, d, J=7.83 Hz), 7.68-7.73 (1H, m), 7.75-7.80 (1H, m), 8.02 (1H, s), 8.68 (1H, t, J=5.68 Hz), 8.98-9.03 (1H, m, J=1.01 Hz), 10.85 (1H, s), 14.03 (1H, s), 14.27 (1H, s). HPLC ret. time (Condition B): 2.913 min.; 97%. LCMS (⁺ESI, M+H⁺) m/z 446. HRMS: calc. 446.1512, found 446.1512.

Example 9

N-(1-(Phenylsulfonyl)azetidin-3-yl)-3-(3-(pyridine-2-ylamino)-1H-pyrazol-5-ylthio)benzamide

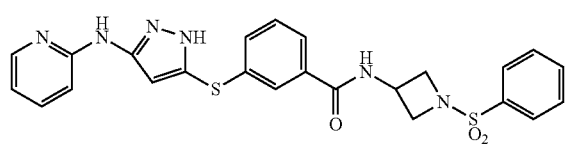

a) Preparation of 3-(3-(pyridine-2-ylamino)-1H-pyrazol-5-ylthio)benzoic acid

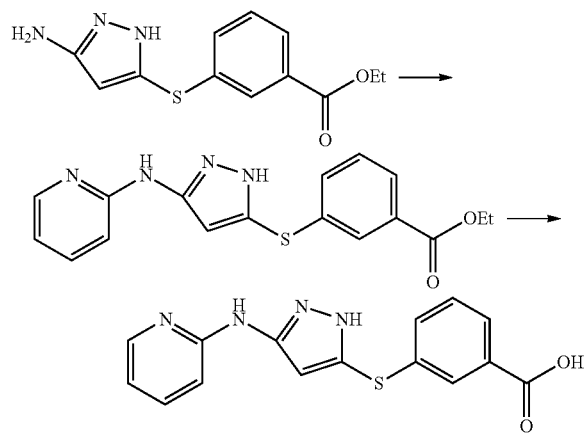

A stirred solution of ethyl 3-(3-amino-1H-pyrazol-5-ylthio)benzoate (0.150 g, 0.57 mmol), 2-chloropyridine (0.130 g, 1.14 mmol) in isopropanol (2 mL) was treated with hydrobromic acid (0.150 mL) and heated at 175° C. in a microwave oven for 30 minutes. The mixture was then diluted with water (1.5 mL) and treated with sodium hydroxide (1 pellet). The reaction was stirred at room temperature overnight, then concentrated to dryness. The residue was dissolved in methanol, acidified with conc. hydrochloric acid and purified on Prep HPLC (MeCN/H₂O/5 mM NH₄OAc) to give the title material (0.113 g, 62%) as a solid. The compound was used as such in the next reaction.

b) Preparation of N-(1-(phenylsulfonyl)azetidin-3-yl)-3-(3-(pyridine-2-ylamino)-1H-pyrazol-5-ylthio)benzamide

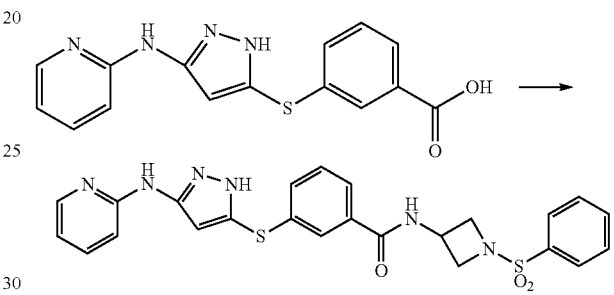

3-(3-(Pyridine-2-ylamino)-1H-pyrazol-5-ylthio)benzoic acid (0.060 g, 0.192 mmol) and tert-butyl 1-(phenylsulfonyl) azetidin-3-ylcarbamate (0.060 g, 0.192 mmol) were treated as described in Example 3, except that the purification was done on Prep HPLC (MeCN/H₂O/0.1% TFA). This afforded the title material (0.049 g, 41%, trifluoroacetic acid salt) as a solid. ¹H NMR 400 MHz DMSO-d₆ δ (ppm): 3.73 (2H, dd, J=8.72, 6.44 Hz), 3.99 (2H, t, J=8.21 Hz), 4.32-4.46 (1H, m), 6.43 (1H, s), 6.99 (1H, t, J=6.19 Hz), 7.20 (1H, d, J=8.59 Hz), 7.32-7.50 (2H, m), 7.59-7.74 (4H, m), 7.75-7.82 (1H, m), 7.82-7.95 (3H, m), 8.21 (1H, d, J=4.55 Hz), 8.98 (1H, d, J=6.06 Hz), 10.76 (1H, s). HPLC ret. time (Condition B): 3.950 min.; 85%. LCMS (⁺ESI, M+H⁺) m/z 507, (⁻ESI M-H⁺) m/z 505, HRMS: calc. 507.1273, found 507.1264.

Example 10

N-(1-(4-Fluorophenylsulfonyl)azetidin-3-yl)-3-(3-(pyridin-2-ylamino)-1H-pyrazol-5-ylthio)benzamide

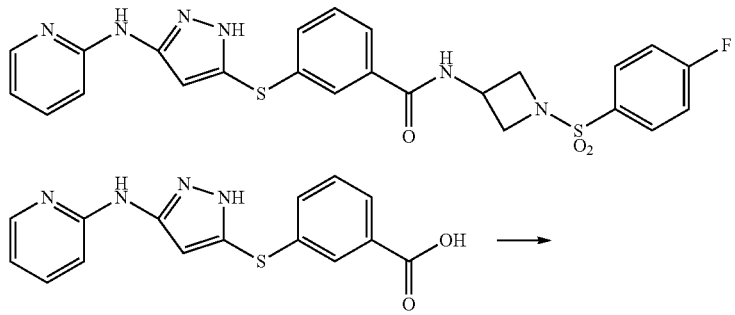

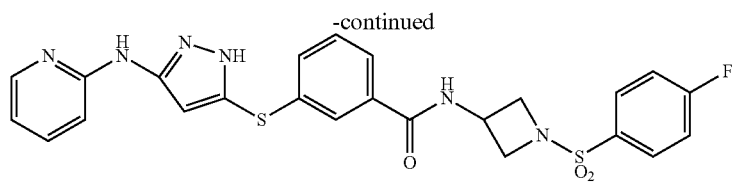

3-(3-(Pyridine-2-ylamino)-1H-pyrazol-5-ylthio)benzoic acid (0.050 g, 0.160 mmol) and tert-butyl 1-(4-fluoro-phenylsulfonyl)azetidin-3-ylcarbamate (0.063 g, 0.19 mmol) were treated as described in Example 3, except that the mixture was purified on Prep HPLC (MeCN/H$_2$O/0.1% TFA). This afforded the title material (0.031 g, 30%, trifluoroacetic acid salt) as a solid. $^1$H NMR 400 MHz DMSO-d$_6$ δ (ppm): 3.72 (2H, dd, J=8.46, 6.44 Hz), 4.00 (2 H, t, J=8.08 Hz), 4.35-4.52 (1 H, m), 6.43 (1 H, s), 6.91-7.03 (1 H, m), 7.18 (1 H, d, J=8.08 Hz), 7.34-7.40 (1 H, m), 7.44 (1 H, t, J=7.71 Hz), 7.50-7.59 (2 H, m), 7.60-7.69 (2 H, m), 7.82-7.98 (3 H, m), 8.20 (1 H, d, J=4.55 Hz), 8.96 (1 H, d, J=6.06 Hz), 10.62 (1 H, br.s). HPLC ret. time (Condition B): 4.125 min.; 91%. LCMS ($^+$ESI, M+H$^+$) m/z 525. HRMS: calc. 525.1179, found 525.1191.

Example 11

Ethyl 3-(3-(3-nitropyridin-2-ylamino)-1H-pyrazol-5-ylthio)benzoate

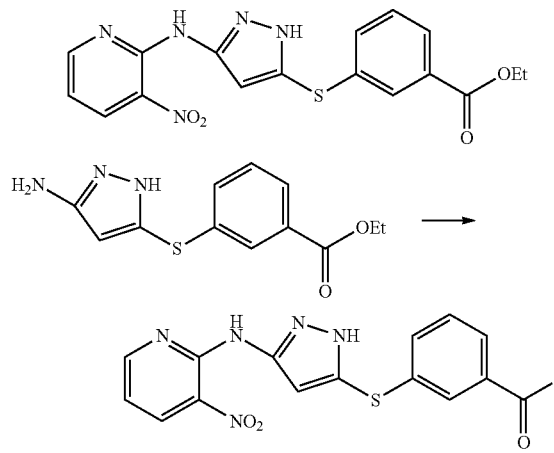

A mixture of 3-(3-amino-1H-pyrazol-5-ylthio)benzoate (0.015 g, 0.057 mmol), 2-chloro-3-nitro-pyridine (0.009 g, 0.057 mmol) and diisopropylethylamine (0.015 mL, 0.086 mmol) in isopropylalcohol (1 mL) was heated at 75° C. for 2 days. The reaction was cooled down and purified by Prep HPLC (MeCN/H$_2$O/5 mM NH$_4$OAc) to give the title material (0.008, 36%) as a solid. $^1$H NMR 400 MHz DMSO-d$_6$ δ (ppm): 1.40 (3H, t, J=7.20 Hz), 4.38 (2H, q, J=7.16 Hz), 6.48 (1H, s), 7.01 (1H, dd, J=8.34, 4.80 Hz), 7.37 (1H, t, J=7.83 Hz), 7.47-7.58 (1H, m), 7.84-7.95 (1H, m), 8.06 (1H, t, J=1.64 Hz), 8.52-8.69 (2H, m), 10.49 (1H, s), 11.51 (1H, br. s). HPLC ret. time (Condition B): 6.300 min.; 100%. LCMS ($^+$ESI, M+H$^+$) m/z 386, ($^-$ESI M–H$^+$) m/z 384.

Example 12

Ethyl 3-(3-(pyrrolo[1,2-f][1,2,4]triazin-4-ylamino)-1H-pyrazol-5-yloxy)benzoate

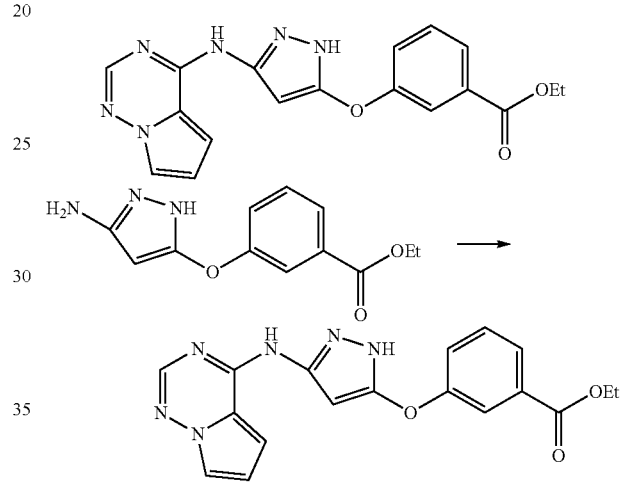

Ethyl 3-(3-amino-1H-pyrazol-5-yloxy)benzoate (0.087 g, 0.35 mmol) and 4-chloropyrrolo[1,2-f][1,2,4]triazine (0.054 g, 0.35 mmol) were reacted as described in Example 1 and afforded the title material (0.037 g, 22%, trifluoroacetic acid salt) as a solid. $^1$H NMR 400 MHz DMSO-d$_6$ δ (ppm): 1.31 (3H, t, J=7.07 Hz), 4.32 (2H, q, J=7.07 Hz), 5.92 (1H, s), 6.78 (1H, dd, J=4.42, 2.65 Hz), 7.09 (1H, s), 7.42-7.48 (1H, m), 7.56 (1H, t, J=7.96 Hz), 7.65-7.67 (1H, m), 7.71-7.76 (1H, m), 7.82 (1H, dd, J=2.27, 1.52 Hz), 8.04 (1H, s), 10.85 (1H, s). HPLC ret. time (Condition A): 1.670 min.; 100%. LCMS ($^+$ESI, M+H$^+$) m/z 365.

We claim:
1. A compound of the formula I

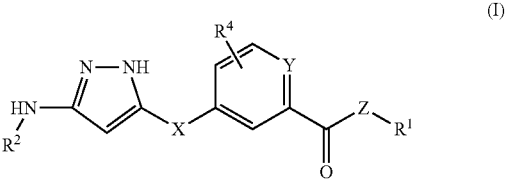

wherein
X is —O— or —S—;
Y is —CH—;
Z is —NH— or —O—;

$R^1$ is H, $C_1$-$C_6$ alkyl, $C_1$-$C_5$ arylalkyl, $C_3$-$C_8$ cycloalkyl, $C_9$-$C_{14}$ bicycloalkyl, $C_6$-$C_{10}$ aryl, $C_5$-$C_{13}$ heteroaryl, $C_4$-$C_{12}$ heterocyclyl and 3 to 8-membered heterocycloalkyl and each of said groups is optionally substituted with 1 to 3 groups selected from the group consisting of halogen, —OH, —C(=O)OR³, —S(=O)NHR³, —SO₂NHR³, —SO₂R³, alkyl, substituted alkyl, —CN, —NHR³, —CONHR³, —OCONHR³, —CONHSO₂R³, —NHCONHR³, —CH₂OR³, —CH₂CH₂OH, alkoxy, substituted alkoxy, aryl, substituted aryl, heteroaryl and substituted heteroaryl;

$R^2$ is an optionally substituted aryl or heteroaryl group; said substituents on the substituted aryl or substituted heteroaryl group are selected from the group consisting of one or more hydrogen, halogen, alkyl, substituted alkyl, alkoxy, substituted alkoxy, hydroxy, halogen, amino, substituted amino, amide, substituted amide and carbamate;

$R^3$ is hydrogen or $C_1$-$C_4$ alkyl; $C_3$-$C_6$ cycloalkyl, $C_6$-$C_{10}$ aryl, substituted aryl, $C_1$-$C_5$ arylalkyl, heteroaryl, heterocyclyl, aryloxy, substituted aryloxy, —CF₃ and —OCF₃; and $R^4$ is hydrogen, alkyl, substituted alkyl, hydroxy, cyano or halogen;

or a pharmaceutically acceptable salt or stereoisomer thereof.

2. A compound of formula II (II)

wherein
X is —O— or —S—;
Y is —CH—;
$R^1$ is H, $C_1$-$C_6$ alkyl, $C_1$-$C_5$ arylalkyl, $C_3$-$C_8$ cycloalkyl, $C_9$-$C_{14}$ bicycloalkyl, $C_6$-$C_{10}$ aryl, $C_5$-$C_{13}$ heteroaryl, $C_4$-$C_{12}$ heterocyclyl and 3 to 8-membered heterocycloalkyl and each of said groups is optionally substituted with 1 to 3 groups selected from the group consisting of halogen, —OH, —C(=O)OR³, —S(=O)NHR³, —SO₂NHR³, —SO₂R³, alkyl, substituted alkyl, —CN, —NHR³, —CONHR³, —OCONHR³, —CONHSO₂R³, —NHCONHR³, —CH₂OR³, —CH₂CH₂OH, alkoxy, substituted alkoxy, aryl, substituted aryl, heteroaryl and substituted heteroaryl;

$R^2$ is an optionally substituted aryl or heteroaryl group; said substituents on the substituted aryl or substituted heteroaryl group are selected from the group consisting of one or more hydrogen, halogen, alkyl, substituted alkyl, alkoxy, substituted alkoxy, hydroxy, halogen, amino, substituted amino, amide, substituted amide and carbamate;

$R^3$ is hydrogen or $C_1$-$C_4$ alkyl; $C_3$-$C_6$ cycloalkyl, $C_6$-$C_{10}$ aryl, substituted aryl, $C_1$-$C_5$ arylalkyl, heteroaryl, heterocyclyl, aryloxy, substituted aryloxy, —CF₃ and —OCF₃; and $R^4$ is hydrogen, alkyl, substituted alkyl, hydroxy, cyano or halogen;

or a pharmaceutically acceptable salt or stereoisomer thereof.

3. A compound of the formula III (III)

wherein
Y is —N— or —CH—;
$R^1$ is H, $C_1$-$C_6$ alkyl, $C_1$-$C_5$ arylalkyl, $C_3$-$C_8$ cycloalkyl, $C_9$-$C_{14}$ bicycloalkyl, $C_6$-$C_{10}$ aryl, $C_5$-$C_{13}$ heteroaryl, $C_4$-$C_{12}$ heterocyclyl and 3 to 8-membered heterocycloalkyl and each of said groups is optionally substituted with 1 to 3 groups selected from the group consisting of halogen, —OH, —C(=O)OR³, —S(=O)NHR³, —SO₂NHR³, —SO₂R³, alkyl, substituted alkyl, —CN, —NHR³, —CONHR³, —OCONHR³, —CONHSO₂R³, —NHCONHR³, —CH₂OR³, —CH₂CH₂OH, alkoxy, substituted alkoxy, aryl, substituted aryl, heteroaryl and substituted heteroaryl;

$R^2$ is an optionally substituted aryl or heteroaryl group; said substituents on the substituted aryl or substituted heteroaryl group are selected from the group consisting of one or more hydrogen, halogen, alkyl, substituted alkyl, alkoxy, substituted alkoxy, hydroxy, hydroxyalkyl, halogen, haloalkyl, haloalkoxy, amino, substituted amino, aminoalkyl, substituted aminoalkyl, alkylamino, substituted alkylamino, amide, substituted amide and carbamate;

$R^3$ is hydrogen or $C_1$-$C_4$ alkyl; $C_3$-$C_6$ cycloalkyl, $C_6$-$C_{10}$ aryl, substituted aryl, $C_1$-$C_5$ arylalkyl, heteroaryl, heterocyclyl, aryloxy, substituted aryloxy, —CF₃ and —OCF₃; and $R^4$ is hydrogen, alkyl, substituted alkyl, hydroxy, cyano or halogen;

or a pharmaceutically acceptable salt or stereoisomer thereof.

4. A compound according to claim 1 selected from the group consisting of
Ethyl 3-(3-(pyrrolo[1,2-f][1,2,4]triazin-4-ylamino)-1H-pyrazol-5-ylthio)benzoate;
3-(3-(Pyrrolo[1,2-f][1,2,4]triazin-4-ylamino)-1H-pyrazol-5-ylthio)benzoic acid;
N-(1-(Phenylsulfonyl)azetidin-3-yl)-3-(3-pyrrolo[1,2-f][1,2,4]triazin-4-ylamino-1H-pyrazol-5-ylthio)benzamide;
3-(3-(Pyrrolo[1,2-f][1,2,4]triazin-4-ylamino)-1H-pyrazol-5-ylthio)benzamide;
tert-Butyl 3-(3-(3-pyrrolo[1,2-f][1,2,4]triazin-4-ylamino)-1H-pyrazol-5-ylthio)benzamido)azetidine-1-carboxylate;
N-(Azetidin-3-yl)-3-(3-(pyrrolo[1,2-f][1,2,4]triazin-4-ylamino)-1H-pyrazol-5-ylthio)benzamide;
N-(1-(4-Fluorophenylsulfonyl)azeticin-3-yl)-3-(3-(pyrrolo[1,2-f][1,2,4]triazin-4-ylamino)-1H-pyrazol-5-ylthio)benzamide;
N-(2-(1H-Imidazol-4-yl)ethyl)-3-(3-(pyrrolo[1,2-f][1,2,4]triazin-4-ylamino)-1H-pyrazol-5-ylthio)benzamide;
N-(1-(Phenylsulfonyl)azetidin-3-yl)-3-(3-(pyridine-2-ylamino)-1H-pyrazol-5-ylthio)benzamide;
N-(1-(4-Fluorophenylsulfonyl)azetidin-3-yl)-3-(3-(pyridin-2-ylamino)-1H-pyrazol-5-ylthio)benzamide;

Ethyl 3-(3-(3-nitropyridin-2-ylamino)-1H-pyrazol-5-ylthio)benzoate; and

Ethyl 3-(3-(pyrrolo[1,2-f][1,2,4]triazin-4-ylamino)-1H-pyrazol-5-yloxy)benzoate;

or a pharmaceutically acceptable salt thereof.

5. A pharmaceutical composition comprising one or more compounds of claim 1 and a pharmaceutically acceptable carrier.

6. A pharmaceutical composition comprising one or more compounds of claim 2 and a pharmaceutically acceptable carrier.

7. A pharmaceutical composition comprising one or more compounds of claim 3 and a pharmaceutically acceptable carrier.

8. A pharmaceutical composition comprising one or more compounds of claim 4 and a pharmaceutically acceptable carrier.

9. A pharmaceutical composition comprising one or more compounds according to claim 1 in combination with a pharmaceutically acceptable carrier and one or more other anti-cancer or cytotoxic agents.

* * * * *

UNITED STATES PATENT AND TRADEMARK OFFICE
CERTIFICATE OF CORRECTION

| | | |
|---|---|---|
| PATENT NO. | : 7,851,500 B2 | Page 1 of 1 |
| APPLICATION NO. | : 12/521061 | |
| DATED | : December 14, 2010 | |
| INVENTOR(S) | : M. Dodier et al. | |

It is certified that error appears in the above-identified patent and that said Letters Patent is hereby corrected as shown below:

Column 38, Line 13:

In Claim 3, after "is" delete "–N– or"

Column 38, Line 29-30:

In Claim 3, after "hydroxy," delete "hydroxyalkyl,"

Column 38, Line 30:

In Claim 3, after "halogen," delete "haloalkyl, haloalkoxy,"

Column 38, Line 31-32:

In Claim 3, after "amino," delete "aminoalkyl, substituted aminoalkyl, alkylamino, substituted alkylamino,"

Signed and Sealed this
Thirteenth Day of September, 2011

David J. Kappos
*Director of the United States Patent and Trademark Office*